US010105088B2

(12) United States Patent
List et al.

(10) Patent No.: US 10,105,088 B2
(45) Date of Patent: Oct. 23, 2018

(54) METHOD FOR PRODUCING AN ANALYTICAL MAGAZINE

(71) Applicant: ROCHE DIABETES CARE, INC., Indianapolis, IN (US)

(72) Inventors: Hans List, Hesseneck-Kailbach (DE); Uwe Krämer, Ilvesheim (DE); Wilhelm Leichner, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 15/051,274

(22) Filed: Feb. 23, 2016

(65) Prior Publication Data

US 2016/0166189 A1 Jun. 16, 2016

Related U.S. Application Data

(60) Division of application No. 13/212,715, filed on Aug. 18, 2011, now Pat. No. 9,301,715, which is a
(Continued)

(30) Foreign Application Priority Data

Feb. 20, 2009 (EP) .................................... 09153210
Aug. 20, 2009 (EP) .................................... 09168336

(51) Int. Cl.
*A61B 5/151* (2006.01)
*B01L 3/00* (2006.01)
(Continued)

(52) U.S. Cl.
CPC ........ *A61B 5/15148* (2013.01); *A61B 5/1411* (2013.01); *A61B 5/150022* (2013.01);
(Continued)

(58) Field of Classification Search
None
See application file for complete search history.

(56) References Cited

U.S. PATENT DOCUMENTS 5,443,080 A 8/1995 D'Angelo et al.
6,036,924 A 3/2000 Simons et al.
(Continued)

FOREIGN PATENT DOCUMENTS

CN 1137746 A 12/1996
CN 200965529 10/2007
(Continued)

OTHER PUBLICATIONS

Banauch et al., A glucose dehydrogenase for glucose determination in body fluids, Z. Klin. Chem. KLin. Biochem, vol. 13, 1975, pp. 101-107.
(Continued)

*Primary Examiner* — Kathryn Wright
(74) *Attorney, Agent, or Firm* — Harness, Dickey & Pierce, P.L.C.

(57) ABSTRACT

A method for producing an analytical magazine is proposed. The analytical magazine is designed to receive a plurality of analytical aids in a plurality of chambers. The method comprises the following steps: providing at least one first component of the analytical magazine, wherein the first component comprises a plurality of receptacles; providing a plurality of analytical aids, wherein the analytical aids are connected to one another and preferably oriented with respect to one another by at least one holding element; introducing the analytical aids into the receptacles; and separating the analytical aids from the holding element.

14 Claims, 6 Drawing Sheets

Related U.S. Application Data continuation of application No. PCT/EP2010/000864, filed on Feb. 12, 2010.

(51) Int. Cl.
*B29C 65/16* (2006.01)
*A61B 5/15* (2006.01)
*G01N 33/487* (2006.01)

(52) U.S. Cl.
CPC ...... *A61B 5/15146* (2013.01); *A61B 5/15151* (2013.01); *A61B 5/15161* (2013.01); *A61B 5/15176* (2013.01); *A61B 5/15186* (2013.01); *A61B 5/150282* (2013.01); *A61B 5/150358* (2013.01); *A61B 5/150412* (2013.01); *A61B 5/150503* (2013.01); *B01L 3/502* (2013.01); *B29C 65/16* (2013.01); *G01N 33/4875* (2013.01); *B01L 2200/12* (2013.01); *B01L 2300/0609* (2013.01); *B01L 2300/0672* (2013.01); *B01L 2300/0825* (2013.01); *B01L 2300/0838* (2013.01); *B01L 2300/0861* (2013.01); *B01L 2300/12* (2013.01); *B01L 2300/16* (2013.01); *Y10T 29/49817* (2015.01); *Y10T 29/49826* (2015.01)

(56) References Cited

U.S. PATENT DOCUMENTS

| | | |
|---|---|---|
| 6,251,083 B1 | 6/2001 | Yum et al. |
| 6,682,490 B2 | 1/2004 | Roy et al. |
| 7,288,073 B2 | 10/2007 | Effenhauser et al. |
| 7,553,615 B2 | 6/2009 | Heindl et al. |
| 7,959,581 B2 | 6/2011 | Calasso et al. |
| 8,234,767 B2 | 8/2012 | Roeper et al. |
| 8,303,518 B2 | 11/2012 | Aceti et al. |
| 9,044,214 B2 | 6/2015 | Beckman et al. |
| 2002/0087056 A1 | 7/2002 | Aceti et al. |
| 2002/0120216 A1 | 8/2002 | Fritz et al. |
| 2002/0188224 A1 | 12/2002 | Roe et al. |
| 2003/0191415 A1 | 10/2003 | Moerman et al. |
| 2003/0199909 A1 | 10/2003 | Boecker et al. |
| 2003/0212347 A1 | 11/2003 | Sohrab |
| 2003/0212423 A1 | 11/2003 | Pugh et al. |
| 2004/0034318 A1 | 2/2004 | Fritz et al. |
| 2004/0092842 A1 | 5/2004 | Boecker et al. |
| 2004/0098009 A1 | 5/2004 | Boecker et al. |
| 2004/0102803 A1 | 5/2004 | Boecker et al. |
| 2005/0027211 A1 | 2/2005 | Kuhr et al. |
| 2005/0033340 A1 | 2/2005 | Lipoma et al. |
| 2005/0214891 A1 | 9/2005 | Horn et al. |
| 2006/0008389 A1 | 1/2006 | Sacherer et al. |
| 2006/0161078 A1 | 7/2006 | Schraga |
| 2006/0178600 A1 | 8/2006 | Kennedy et al. |
| 2006/0184064 A1 | 8/2006 | Paasch et al. |
| 2006/0200044 A1 | 9/2006 | Freeman et al. |
| 2006/0264996 A1 | 11/2006 | LeVaughn et al. |
| 2007/0016103 A1 | 1/2007 | Calasso et al. |
| 2007/0038150 A1* | 2/2007 | Calasso ............... A61B 5/1411 600/583 |
| 2007/0041869 A1 | 2/2007 | Zimmer |
| 2007/0100255 A1 | 5/2007 | Boecker et al. |
| 2007/0129650 A1 | 6/2007 | Freeman et al. |
| 2007/0142748 A1 | 6/2007 | Deshmukh et al. |
| 2007/0142854 A1 | 6/2007 | Schraga |
| 2007/0167872 A1 | 7/2007 | Freeman et al. |
| 2007/0173741 A1 | 7/2007 | Deshmukh et al. |
| 2007/0278097 A1 | 12/2007 | Bhullar et al. |
| 2007/0292314 A1 | 12/2007 | Effenhauser et al. |
| 2008/0021346 A1 | 1/2008 | Haar et al. |
| 2008/0039887 A1 | 2/2008 | Conway et al. |
| 2008/0040919 A1 | 2/2008 | Griss et al. |
| 2008/0070272 A1 | 3/2008 | Franciskovich et al. |
| 2008/0094804 A1 | 4/2008 | Reynolds et al. |
| 2008/0103415 A1 | 5/2008 | Roe et al. |
| 2008/0213809 A1 | 9/2008 | Heindl et al. |
| 2008/0243032 A1 | 10/2008 | Hindelang et al. |
| 2008/0294068 A1 | 11/2008 | Briggs et al. |
| 2008/0300509 A1 | 12/2008 | Hoenes et al. |
| 2009/0010802 A1 | 1/2009 | Joseph et al. |
| 2009/0093695 A1 | 4/2009 | Nakamura et al. |
| 2009/0099477 A1 | 4/2009 | Hoenes et al. |
| 2009/0099585 A1 | 4/2009 | Conway et al. |
| 2009/0192411 A1 | 7/2009 | Freeman |
| 2009/0204025 A1 | 8/2009 | Marsot et al. |
| 2010/0010375 A1 | 1/2010 | Haar et al. |
| 2010/0174211 A1 | 7/2010 | Frey et al. |
| 2010/0185120 A1 | 7/2010 | Sacherer et al. |
| 2010/0222799 A1 | 9/2010 | Roeper et al. |
| 2010/0234869 A1 | 9/2010 | Sacherer |
| 2011/0077554 A1* | 3/2011 | Roe ................... A61B 5/1411 600/583 |
| 2011/0143416 A1 | 6/2011 | Horn et al. |
| 2012/0039772 A1 | 2/2012 | Hoenes |
| 2012/0041339 A1 | 2/2012 | Kuhr et al. |
| 2012/0063970 A1 | 3/2012 | List et al. |

FOREIGN PATENT DOCUMENTS

| | | |
|---|---|---|
| DE | 19819407 A1 | 11/1999 |
| EP | 1360932 A1 | 11/2003 |
| EP | 1360935 A1 | 11/2003 |
| EP | 1900321 A1 | 3/2008 |
| EP | 1929937 A1 | 6/2008 |
| EP | 1997429 A1 | 12/2008 |
| EP | 2042098 A1 | 4/2009 |
| EP | 2050392 A1 | 4/2009 |
| JP | 2005510336 A | 4/2005 |
| JP | 2006187624 A | 7/2006 |
| WO | 0164105 A1 | 9/2001 |
| WO | 2002101343 A2 | 12/2002 |
| WO | 03070099 A1 | 8/2003 |
| WO | 2003088834 A1 | 10/2003 |
| WO | 2004041082 A1 | 5/2004 |
| WO | 2005018915 A1 | 3/2005 |
| WO | 2005065414 A2 | 7/2005 |
| WO | 2005104948 A1 | 11/2005 |
| WO | 2006031920 A2 | 3/2006 |
| WO | 2007001003 A1 | 1/2007 |
| WO | 2008145625 A2 | 12/2008 |
| WO | 2009036986 A2 | 3/2009 |

OTHER PUBLICATIONS

Bergmeyer, Methoden der enzymatischen Analyse (Methods of enzymatic analysis), Verlag Chemie, 2nd edition, 1970, p. 417.
Hoenes et al., The Technology Behind Glucose Meters: Test Strips, Diabetes Technology & Therapeutics, vol. 10, Supplement 1, 2008, pp. S-10-S26.
Translation of First Office Action dated Feb. 1, 2018 in Chinese Patent Application No. 201610107351.1, filed Feb. 12, 2010.

* cited by examiner

METHOD FOR PRODUCING AN ANALYTICAL MAGAZINE

CROSS-REFERENCE TO RELATED APPLICATIONS

This application is a divisional of U.S. patent application Ser. No. 13/212,715, filed on Aug. 18, 2011, issued as U.S. Pat. No. 9,301,715 on Apr. 5, 2016, which is a continuation of International Application No. PCT/EP2010/000864, filed on Feb. 12, 2010, which claims the benefit and priority of European Patent Application Nos. 09153210.1, filed on Feb. 19, 2009 and 09168336.7, filed on Aug. 20, 2009. The entire disclosures of each of the above applications are incorporated herein by reference.

BACKGROUND

The present invention relates to a method for producing an analytical magazine which is designed to receive a plurality of analytical aids. The invention furthermore relates to an analytical magazine. Analytical magazines of this type are used in medical diagnostics, in particular, in order to qualitatively or quantitatively detect one or more analytes in body fluids. By way of example, said analytes can be metabolites, for example blood glucose.

In the field of diagnostics it is necessary in many cases to obtain samples of body fluid, in particular blood samples or samples of interstitial fluid, in order to be able to detect constituents therein, in particular specific analytes. Examples of such analytes are blood glucose, coagulation parameters, triglycerides, lactate or the like. In accordance with the detected concentrations, a decision can then be taken about a corresponding treatment, for example.

In the diagnostic methods mentioned, generally one or a plurality of analytical aids are used in order to obtain and/or analyze the samples of body fluid. Thus, the analytical aids can comprise lancets, for example, that is to say elements which are designed to produce an opening in a subject's skin, through which the body fluid can be drawn. As an example of such lancets, reference may be made to WO 02/36010 A1 (see also, US 2004/0034318).

Furthermore, the analytical aids can comprise one or a plurality of test elements with test chemicals which are designed to change specific detectable properties under the action of the analyte to be detected. By way of example, said analytes may comprise electrochemically detectable properties or the changes thereof and/or optically detectable properties. For such test chemicals, too, reference may be made to the prior art, for example J. Hones et al., Diabetes Technology & Therapeutics, Volume 10, Supplement 1, 2008, page 10 to page 26.

In addition, integrated test elements are also known which are used both for the purpose of producing a sample of body fluid and for the purpose of transporting the sample and, if appropriate, even for the purpose of qualitative and/or quantitative analysis of said sample. Examples of such analytical aids are so-called microsamplers, in which, by means of a lancet, a puncture or incision is produced, the sample is taken and is transported to one or a plurality of test fields with the test chemical. Said test fields can be arranged separately from the lancet, but can also be part of the lancet itself. Systems of this type, which are described for example in US 2004/0193202 A1, US 2008/0249435 A1 or in WO 03/009759 A1 (see also U.S. Pat. No. 7,288,073), are particularly user-friendly owing to their high degree of integration.

One technical challenge in providing analytical systems and analytical aids, however, consists in providing them in large quantities under suitable conditions. Thus, they generally have to be provided in such a way that the analytical aids are stored under sterile conditions, for example by means of corresponding seals. At the same time, however, the seals must not impair the quality of the analytical aids and must not make it more difficult to use said analytical aids. For this purpose, the analytical aids are generally provided by means of corresponding magazines, which are also referred to as hereinafter as analytical magazines. For systems which are intended to carry out for example a capillary blood analysis fully automatically without the subject's intervention, a multiplicity of lancets and also a multiplicity of test elements, for example each with one or more test chemicals, may be present for example in a magazine of this type.

A multiplicity of different analytical magazines are known from the prior art. In principle, it is possible, independently of the type of analytical aid, to distinguish between three main types of magazines, namely round magazines (for example in the form of drums and/or disks), linear magazines (for example in the form of stack magazines, zigzag magazines or the like) and tape magazines, in which the analytical aids are arranged on a tape or some other form of at least partly flexible carrier. These types of magazines can, in principle, also be used, or modified, in the context of the invention described below. In the prior art, round magazines are described for example in US 2006/0008389, US 2007/0292314, US 2006/0184064, US 2003/0212347 or US 2002/0087056. Linear magazines are described for example in U.S. Pat. No. 6,036,924 or US 2003/0191415. Tape magazines are described for example in US 2002/0188224, in US 2008/0103415, in EP 1360935 A1 or in DE 19819407 A1.

Generally, the disadvantage in the case of analytical magazines, in particular integrated analytical magazines with combined analytical aids with lancet function and test element function, consists in ensuring freedom from contamination and sterility. By way of example, one difficulty is that each set composed of lancet and test element has to be kept separate from the respective other sets since at least the lancets have to be kept sterile until immediately before they are used.

However, these requirements in turn increase the outlay for the production of the analytical magazines. Owing to the different natures of lancets and test elements, the history of origination thereof is extremely different. Consequently, these elements of the system are generally provided in different forms of presentation for the assembly of the overall analytical magazine. These requirements mean that in practice analytical magazines generally have to be filled individually. Thus, by way of example, the lancets and the test elements have to be inserted individually into the analytical magazines and/or into individual chambers of the analytical magazines, which generally requires a high outlay in respect of apparatus. One exception in this regard is constituted only by tape-based systems, in which the individual elements can firstly be applied individually to a carrier tape and, having been wound up onto said carrier tape, can then be introduced into a magazine. In any event, however, the individual analytical aids have to be applied piece by piece, which requires a considerable production outlay.

SUMMARY

Therefore, it is an object of the present invention to provide methods and devices which at least substantially avoid the disadvantages of known methods and devices. In particular, the method proposed is intended to enable production of analytical magazines in the case of which the outlay in respect of apparatus and hence the total outlay for the production of the analytical magazines can be considerably reduced, without the quality of the analytical magazines and/or of the analytical aids thereby being impaired.

This object is achieved by means of the methods and devices comprising the features of the independent claims. Advantageous developments of the invention, which can be realized individually or in combination, are presented in the dependent claims. A method for producing an analytical magazine and also an analytical magazine are proposed, wherein the analytical magazine may be producible in particular using a production method according to the invention. Accordingly, with regard to possible configurations of the analytical magazine and individual aspects of the analytical magazine, reference may be made to the description of the method, and vice versa.

The analytical magazine is designed to receive a plurality of analytical aids in a plurality of chambers. Consequently, an analytical magazine should be understood to mean a device which can be handled as a unit, which can have a common housing, for example, and which can generally be usable in medical technology. In this case, analytical should generally be understood to mean the possibility of use for the qualitative and/or quantitative detection of at least one analyte and/or the determination of at least one further measurable property. In this regard, reference may be made to the above description, for example. In particular, analytical may thus be understood to mean a diagnostic property, that is to say a use for determining at least one property of a body and/or of part of a body of a subject. The analytical magazine can accordingly be used in an analytical system which thus becomes an analytical system according to the invention. By way of example, such a system can be a measuring device by means of which at least one analyte, for example at least one metabolite, in a body fluid of the subject is detected qualitatively and/or quantitatively. By way of example, these systems can be blood glucose measuring devices.

Analytical aids should generally be understood to mean, in the context of the present invention, aids which can be used supportively in the case of the analytical functions described above. In particular, the analytical aids can be medical and/or diagnostic aids, in particular aids which are designed to be used in the case of a qualitative and/or quantitative detection of at least one analyte, for example one or more of the abovementioned analytes, in a subject's body fluid, for example blood, interstitial fluid, urine or similar body fluids. In particular, the analytical aids can be configured as disposable aids (disposables), that is to say be intended for single use. The analytical aids can accordingly comprise for example at least one lancet, that is to say an element which is designed to produce at least one opening in the subject's skin, for example an ear lobe, a finger pad, or a forearm of the subject. By way of example, said lancets can comprise one or more puncturing elements, with needle tips and/or sharpened tips. Other sharp-edged elements can also be used alternatively or additionally, for example blades, sharp-edged tips or the like. The lancets can be produced for example from bar-type starting materials, for example in the form of needle-type lancets. However, the use of one or more lancets produced from plate-type materials, in particular metal sheets, is particularly preferred in the context of the present invention. This will be explained in greater detail below.

As an alternative or in addition to lancets, the analytical aids can also each comprise one or a plurality of test elements. These test elements have at least one test chemical which is designed to change at least one measurable property in the presence of at least one analyte to be detected. Said test chemical, designed to indicate the presence or—which is intended to be encompassed thereby—the absence of the at least one analyte by itself or in interaction with the analyte and/or further auxiliary materials, can be configured in various ways. In this regard, reference may for example again be made to the article by J. Hones et al. cited above. Furthermore, reference may be made to WO 2007/012494 A1 (see also, US 2008/0213809), for example, which describes particularly moisture-stable test chemicals. The test chemicals mentioned in these documents can also be used, individually or in combination, in the context of the present invention. In particular, it is possible to use strongly specific test chemicals, in the case of which the detection reacts specifically to the at least one analyte. The at least one measurable property, from the measurement of which the at least one analyte can be detected qualitatively or quantitatively, can comprise for example at least one electrochemical property and/or at least one optical property. By way of example, as is explained in greater detail below, the test chemical can be embodied in the form of one or more test fields.

Furthermore, the analytical aids can also be configured in such a way that they are configured as combined test elements. Thus, by way of example, combined test elements with at least one lancet and at least one test chemical can be used, wherein the test chemical can be designed to change at least one measurable property in the presence of the at least one analyte to be detected. By way of example, the test element can be integrated directly into the lancet. Thus, by way of example, the test chemical can be taken up at the end of the lancet and/or cover parts of the lancet. Alternatively or additionally, however, it is also possible for the lancet and the test element to be formed separately, for example in each case at least one lancet and in each case at least one test element per chamber of the analytical magazine. These parts of the analytical aid may for example also be handled separately, such that, by way of example, the lancet can be handled by an actuator of a system in order to perform a puncturing movement and/or collecting movement, while the test element for example remains unchanged, for example within the chamber. Thus, by way of example, the system can be designed to carry out a puncturing and/or collecting movement by means of the at least one lancet and/or a capillary element optionally contained in the lancet, such that body fluid can be taken up by the lancet directly during a puncturing operation and/or during a sampling movement. In this case, firstly a puncture into the subject's skin can be produced, body fluid can be collected and the latter can then be transferred to the test element, for example during a backward movement of the lancet, back into the chamber. Other configurations are also possible.

As an alternative or in addition to lancets and/or test elements, the analytical aids can comprise further elements which are used for an analysis purpose. Thus, by way of example, transfer elements and/or collecting elements may be included, which serve the purpose of taking up and/or transporting body fluid. By way of example, such transport elements and/or collecting elements can be used to take up blood and/or interstitial fluid from the subject's skin and/or a location within the subject's body and/or a location on the subject's skin and/or to effect transport to a test element, in particular one or more test fields. Such transport can be effected by a transport movement, for example, by means of one or more transport elements which are configured in movable fashion and can take up and transfer a quantity of the sample of body fluid. Alternatively or additionally, other transport elements and/or collecting elements may also be provided, for example capillaries and/or elements with capillary action. By way of example, closed capillaries or capillary channels, in particular capillary gaps, may be involved in this case. Combined analytical aids having at least one lancet function and at least one capillary function are also referred to hereinafter as microsamplers.

As explained above, it is particularly preferred for the analytical aids to be received in the chambers in such a way that exactly one analytical aid is received in one chamber. If the analytical aid itself comprises in each case a plurality of analytical sub-aids, such as, for example, in each case at least one lancet and in each case at least one test element, then it is possible, by way of example, for the in each case at least one test element and/or the in each case at least one lancet which are provided for a single, common test (for example a single taking-up of body fluid and/or analysis of body fluid) to be received in a common chamber. This configuration, in which one chamber receives respectively one analytical aid, for example with in each case at least one sub-aid in the form of a test element and/or with in each case at least one sub-aid in the form of a lancet, can be realized particularly in the case of a disk-shaped magazine, or else in the case of other designs of magazines, such as rod-shaped magazines, for example. As an alternative to a configuration in which each analytical aid is received in a separate chamber, a configuration in which a plurality of analytical aids of identical type or of different types are received in one chamber is also possible. One example of such a configuration is a tape magazine in which a good winding with a plurality of unused analytical aids is received in a first chamber and a poor winding with a plurality of used analytical aids is received in a second chamber. Other configurations are also possible.

In this case, a chamber should generally be understood to mean an element which has at least one at least partly closed cavity in which the analytical aid can be received. In this case, the cavity can also comprise one or more openings, as will be explained in greater detail below. The chambers can also comprise in each case one or more sub-chambers and can comprise in each case one or more chamber walls facing an interior of the chambers.

The method for producing the analytical magazine comprises the method steps described below. The method steps are preferably, but not necessarily, carried out in the order presented. Other orders are also possible, in principle. Furthermore, the method can comprise additional method steps not described. Furthermore, individual or a plurality of method steps can be carried out repeatedly and/or can be carried out temporally in parallel and/or in temporally overlapping fashion.

In a first method step, at least one first component of the analytical magazine is provided. Said first component can comprise for example a component of a housing of the analytical magazine. By way of example, the component can be configured such that it is stiff at least in part. The process of providing can be effected manually and/or automatically, for example. In this case, the first component has a plurality of receptacles. By way of example, in each case at least one receptacle can be provided for each of the abovementioned chambers, said at least one receptacle being assigned to the respective chamber. Said receptacles can comprise for example depressions, rails, grooves, slots, webs, walls, projections or similar elements which are able at least in part to fix the analytical aids and/or parts of said analytical aids and/or to prevent, within predetermined limits, a change in the position and/or orientation of said analytical aids. The receptacles can also be part of the subsequent chambers, for example in the form of sub-chambers, for example upwardly open sub-chambers or chambers which are closed off in a subsequent method stage, for example, in particular by means of a further component, for example by means of a cover. By way of example, the receptacles can comprise depressions which subsequently constitute a part of the walls of the chambers.

In a further method step, a plurality of analytical aids of the type described above are provided. If the analytical aids respectively received in a chamber consist in each case of different types of analytical sub-aids, then these sub-aids can be provided in each case in different method steps and/or also be provided jointly with all or some further sub-aids. The process of providing can in turn be effected for example manually or else in wholly or partly automated fashion.

In contrast to the prior art, however, the proposed production method in accordance with a first aspect of the present invention proposes that the analytical aids not be provided and inserted into the magazine piece by piece, rather that they be provided and inserted into the magazine preferably all at once. In this case, all the chambers can be loaded simultaneously with the analytical aids and/or, this being intended to be equivalent, with sub-aids if the analytical aids are in each case composed per se of a plurality of sub-aids. At the very least, a plurality of chambers should be loaded simultaneously with at least one type of analytical aid and/or a sub-aid, preferably all the chambers. The outlay on assembly can thereby be considerably reduced.

Accordingly, it is proposed that the analytical aids (or, equivalently, the sub-aids) provided be connected to one another and preferably oriented with respect to one another by at least one holding element. The process of providing can then be effected in this connected and preferably oriented form. In this case, a holding element should generally be understood to mean an element which is suitable for jointly providing the plurality of analytical aids. Examples of this holding element are described in greater detail below. In this case, an orientation of the analytical aids with respect to one another can be understood to mean, for example, at least substantial fixing of an absolute position and/or a spatial orientation (for example an angular orientation) of the analytical aids with respect to one another. In this case, slight deviations are also possible, however, which may lie within the scope of predetermined tolerances, for example, which may be predetermined for example by the tolerances of the process of receiving the analytical aids in the chambers.

In a further method step, the analytical aids or, this being intended to be equivalent in the context of the present invention, the sub-aids are introduced into the receptacles. This process of introducing can be effected for example by simple laying in, inserting or the like and can for example in turn be effected manually or else in at least partly automated fashion. In this case, in a manner corresponding to the process of providing the plurality of analytical aids, the process of introducing can be effected at least substantially simultaneously for a plurality or preferably all of the chambers, that is to say substantially in one method step for all the analytical aids or sub-aids provided in the previously described step.

In a further method step, the analytical aids are then separated from the holding element. The process of separating can preferably be effected wholly or partly after and/or during the process of introducing the sub-aids into the receptacles. In this case, separating during the process of introducing should be understood to mean separating during one or a plurality of method steps that are necessary in order to be able to introduce the sub-aids into the receptacle. The production of the sub-aids may substantially be concluded at this point in time, such that they may still be connected at this point in time. The separation can then be effected directly before and/or during these method steps and/or at a point in time at which the sub-aids have already been introduced in part into the receptacle and/or at a point in time at which the sub-aids have already been completely introduced into the receptacle. As an alternative or in addition, however, complete or partial separation can also be effected during and/or before the process of introducing into the receptacles. In this case, it is possible to use a fixing device, for example, in order to fix the analytical aids and/or sub-aids temporarily after separation before they are introduced into the receptacles. The process of separation can be effected by conventional separating methods, for example, which may in particular also be adapted to the manner in which the analytical aids or sub-aids are connected to the holding element. By way of example, breaking methods, cutting methods (in particular laser cutting methods and/or mechanical cutting methods), stamping methods, chemical separating methods or combinations of the stated and/or other separating methods can be used for this process of separating, as will be explained in even greater detail below.

The method proposed has a large number of advantages over known methods. The great simplification of the outlay for production should be mentioned as the principal advantage. Thus, by way of example, analytical magazines in which the analytical aids are preferably arranged separately from one another in different chambers can be produced with extremely little outlay. The analytical aids may be handled for example wholly or in part independently of one another, that is to say independently of the analytical aids received in the other chambers, in contrast for example to analytical aids that are received on tapes. Nevertheless, the outlay for loading the individual chambers with analytical aids can be considerably reduced by the method proposed, since the individual chambers now no longer need to be loaded individually. Thus, it is now possible for groups of chambers and/or all chambers to be loaded simultaneously. These advantages are achieved without accepting disadvantages with regard to losses of quality, since the sterility of the individual chambers can be ensured for example by corresponding seals described in even greater detail below.

The method proposed can be advantageously developed in various ways. Thus, the at least one first component of the analytical magazine is preferably configured as a substantially rigid component, that is to say as a component which is not subjected to any significant flexure and/or other deformations at least under the action of its own weight. Accordingly, the above-described receptacles are preferably arranged in a fixedly predetermined alignment and/or orientation with respect to one another. Accordingly, as explained above, it is also possible for the at least one holding element to be configured preferably in substantially rigid fashion.

The analytical magazine can, in principle, comprise the plurality of chambers in any desired arrangement with respect to one another. Thus, by way of example, rod magazines, series magazines, zigzag magazines or the like are conceivable. In particular, reference may be made to the abovementioned types of magazines. It is particularly preferred for the analytical magazine to have a disk form, in particular a form of a circular disk and/or an annular disk. Accordingly, the chambers and/or the receptacles can be arranged in the disk-shaped analytical magazine substantially in radial orientation. By way of example, it is possible to configure the analytical magazine in the form of the circular disk and/or annular disk in such a way that a sampling movement can be carried out by means of the analytical aids and/or by means of at least one of the analytical aids received in each chamber and/or by means of at least one sub-aid. A sampling movement may be understood to mean, for example, a puncturing movement and/or a collecting movement for producing and/or collecting and/or transferring a sample and/or part of a sample of body fluid. Accordingly, this sampling movement can be effected in a radial direction, for example. For this purpose, at least one opening can be provided for example in the case of the annular disk inside the magazine, for example at least one actuator and/or part of an actuator system of an analytical system engaging into said at least one opening in order to be able to couple to the analytical aids and/or sub-aids in each chamber (for example successively) and to carry out the sampling movement. For the coupling, reference may be made for example to the prior art cited above, for example WO 02/36010 A1 (see also, US 2004/0034318). However, other types of coupling are also possible, in principle. Exemplary embodiments of circular-disk-shaped and/or annular-disk-shaped magazines are described in greater detail below.

Accordingly, the at least one holding element can also be adapted to the configuration of the magazine. Thus, by way of example, in the case of a rod-shaped magazine, the holding element can be configured for providing the analytical aids in a parallel arrangement with respect to one another. In the case of a circular-disk-shaped and/or annular analytical magazine the holding element can be configured for example for providing the analytical aids in a radial orientation with respect to one another. By way of example, as explained above, the analytical aids can comprise lancets and/or microsamplers as analytical aids and/or sub-aids, which can be provided for example by means of the holding element in a radial orientation with respect to one another, that is to say a radiate orientation with respect to one another, for example in an equidistant arrangement. This process of providing can be effected for example in such a way that the tips of said lancets and/or microsamplers in each case point radially outward.

The holding element can, in principle, be constructed comparatively complexly and can comprise a multiplicity of sub-elements, for example. Accordingly, the holding element can be configured for a plurality of loading processes. It is particularly preferred, however, for the holding element to be configured as a disposable holding element configured for exactly one loading process or a limited number of loading processes. Accordingly, it is particularly preferred for the holding element to be configured comparatively simply, for example as an integral holding element. In particular, the analytical aids can be worked wholly or in part from a basic material of the holding element. By way of example, this can be a metallic basic material from which analytical aids in the form of lancets and/or micro samplers, for example, are worked in one or a plurality of work steps, thus giving rise to the actual holding element and the analytical aids or parts thereof. For the working process it is possible in this case to use, in principle, any desired, for example mechanical and/or chemical methods, for example etching methods and/or cutting methods and/or laser methods. The holding element can comprise at least one simple disk, for example, that is to say a planar, substantially plate-shaped element whose lateral extents exceed its thickness by a multiple. By way of example, the disk-shaped element can comprise a simple metal disk. By way of example, said metal disk can be configured as a substantially rectangular and/or round metal disk, which is preferred particularly in the case of the configuration of the analytical magazine as a round analytical magazine, in particular with a radial orientation of the analytical aids. By way of example, the analytical aids can be worked wholly or in part from said disk, such that the analytical aids are formed and the remaining disk forms the holding element or a part thereof.

The analytical aids can be produced in particular integrally with the holding element. This is preferred in particular when the holding element is configured as a disposable holding element. In this case, the analytical aids can be configured completely or in part integrally with the holding element. If a plurality of sub-aids are provided per analytical aid, then one, a plurality or all of said sub-aids can be configured integrally with the holding element.

The integral configuration can be effected, for example by virtue of the fact that the analytical aids or, this being intended to be equivalent, sub-aids can be worked from a blank element of the holding element in one or a plurality of production steps. Said blank element can for example in turn comprise a plate-shaped element, in particular a disk-shaped element, for example a metal disk. The process of working the analytical aids or sub-aids can be effected for example by known work steps, in particular etching processes. Thus, lancets, in particular, can also be worked from the blank element of the holding element for example by means of one or more etching processes. The use of at least one etching process is advantageous for other analytical aids or sub-aids as well. As an alternative or in addition to etching processes, however, other types of production processes can also be used, in particular for working the analytical aids or sub-aids from the blank elements, for example cutting processes, stamping processes or the like.

A further, very efficient form of holding elements is a holding element in the form of a long strip or comprising a long strip, which comprises a multiplicity of arrangements of analytical aids and/or sub-aids, for example lancets and/or microsamplers. This permits roll-to-roll processing, for example.

As explained above, the process of separating the analytical aids or sub-aids from the holding element can be effected using one or a plurality of corresponding separating methods. As explained above, a breaking method, in particular, is preferred. For this breaking method, but also for other types of separating methods, it is preferred if, prior to separating the analytical aids from the holding element, at least one connection is provided between the analytical aid and the holding element. Said connection can be adapted to the particular use of the at least one separating method. By way of example, said connection can comprise at least one bridge and/or at least one other connecting element, which is preferably likewise configured integrally with the holding element and/or the analytical aids. Said connection can preferably comprise at least one desired breaking location, particularly when at least one breaking method is used. The desired breaking location can comprise for example a tapered portion and/or a scribed portion and/or some other type of weakening of a material thickness of the connecting element. A targeted reduction of the material strength or an embrittlement in the region of the desired breaking location is also possible, for example a targeted production of glass hardness in an otherwise tough elastic steel, for example by means of a laser. Preferably, the connection is configured in such a way that after its separation or after the analytical aids have been separated from the holding element, substantially no disturbing residues which might subsequently impair the function of the analytical aid remain on the analytical aid, for example the lancet. It can thus be ensured by means of the abovementioned tapered portions and/or desired breaking locations, for example, that a clean break arises, such that, by way of example, sliding of the lancets and/or of other analytical aids and/or sub-aids for a sampling movement is not impaired. In particular, a desired breaking location can be configured in such a way that it is offset inward from an edge of the analytical aid, for example into a waist of the analytical aid. This has the advantage that breaking residues that remain, if appropriate, when the analytical aid is separated from the holding element, do not impede sliding of the analytical aid in the chamber.

Generally, it is preferred if the chambers and/or the analytical aids are configured in such a way that the analytical aids are mounted such that they are movable wholly or in part for a sampling movement. In this case, the movable mounting can be effected for the analytical aid as a whole or else for just one or a plurality of sub-aids of the analytical aids, for example one or more lancets, while test elements, for example, can remain fixedly within the chambers and/or at other locations of the analytical magazine. The movable mounting can be effected for example in such a way that the analytical aids, as will be explained in even greater detail below, are fixed completely or in part while the analytical aids are stored in the chambers of the magazine, whereas this fixing is released and/or overcome for a sampling movement. The sampling movement can be effected, as explained above, for example by an analytical system that interacts with the analytical magazine and/or comprises the analytical magazine, for example a measuring device, which, by way of example, can have one or a plurality of corresponding actuators. These actuators may be designed to interact with the analytical aids in the chambers and/or with sub-aids of said analytical aids and to couple to them, preferably individually. These actuators, which may also comprise parts of the magazine itself, may comprise for example corresponding coupling elements and/or sampling elements by means of which the couplings and/or sampling movements can be carried out, for example one or more grippers, hooks, plungers, slides or combinations of the stated and/or other elements. Preferably, the sampling movement and/or the system may be designed in such a way that the sampling movement comprises a movement toward the subject's skin, if appropriate including a puncturing movement in the subject's skin, followed by a movement back, away from the subject's skin. By way of example, the movement back may comprise a re-magazining, that is to say a movement during which the at least one analytical aid or sub-aid is once again received completely or in part in the chamber and/or some other chamber of the analytical magazine. In this way, entirely satisfactory disposal of the analytical aids from a hygiene standpoint can be ensured.

As explained above, the method can comprise further method steps. Thus, by way of example, the analytical magazine can comprise further components besides the first component. It is particularly preferred, however, if, apart from the analytical aids and the at least one first component, a smallest possible number of further components is provided, for example a number of one, two, three or preferably at most four further components. In this way, production of the analytical magazine in the simplest possible manner can be ensured.

The method can comprise, in particular, at least one further method step, in which at least one second component is applied. Said second component can for example in turn be a component of a housing of the analytical magazine. The second component can be applied to the at least one first component for example directly or indirectly. Thus, the first component can be configured for example, as explained above, as a base part of a housing, whereas the second component is configured for example as a cover part of the housing, or vice versa. Other configurations are also possible. The second component can be applied to the first component for example with the interposition of further components. In this case, the first component and the second component can be connected to one another by one or more connections, for example force-locking and/or positively locking and/or cohesive connections. Particular preference is given to cohesive connections, for example in the form of adhesive-bonding connections and/or welding connections, in particular by laser welding and/or ultrasonic welding.

In the step of applying the at least one second component, in particular to the first component, the chambers can for example be formed or developed. These chambers may arise for example by virtue of the fact that the abovementioned receptacles in the first component form partial walls of the chambers, whereas parts of the second component form further partial walls of the chambers. The second component, too, can accordingly comprise for example depressions and/or similar constituent parts of the chambers which subsequently form part of the chambers. The chambers preferably formed or developed by the process of applying the at least one second component may, after the second component has been applied, also still be present in a manner such that they are open in part, for example with one or a plurality of openings, which will also be described in detail below. In particular, during the process of applying the at least one second component, the receptacles of the first component with the analytical aids or sub-aids of the analytical aids received therein can be at least substantially closed off. In this case, a process of at least substantially closing off should be understood to mean a process in which the spatial boundaries of the chambers are at least substantially defined. As explained above, in this case it is possible, however, for one or more openings to remain, in particular in the chamber walls. By way of example, at least one sampling opening can be provided, for example on a side of the magazine which faces the subject when the analytical magazine or the analytical system is used, for example an outer circumferential side of a circular-disk-shaped and/or annular magazine. Through these sampling openings, where for example at least one sampling opening of this type can be provided per chamber, the analytical aids and/or sub-aids can emerge from the chambers, for example in order to carry out the sampling movements mentioned above. As an alternative or in addition to sampling openings, actuator openings can be provided, for example at least one actuator opening per chamber. These actuator openings can be configured in order that an actuator and/or a part of an actuator, in particular of an actuator of the analytical system, can penetrate completely or in part into the chambers in order to excite the at least one analytical aid to effect a sampling movement or in order to carry out a sampling movement by means of said analytical aid or sub-aid. These actuator openings can be provided for example on an opposite side with respect to the sampling openings, for example a side of the magazine which is remote from the subject's skin surface, for example an inner circumference of an annular disk. As an alternative or in addition, however, the actuator openings can also be provided at side surfaces of the chambers, depending on the type of coupling of the actuator to the analytical aids.

As an alternative or in addition to the at least one sampling opening and/or the at least one actuator opening, measurement openings can furthermore be provided, for example in each case at least one measurement opening per chamber. Through these measurement openings, it is possible, for example, to perform measurements on the optional test elements received completely or in part in the chambers, for example optical and/or electrical measurements. By way of example, the measurement openings can comprise measurement windows, which can be configured as open or else closed off with a transparent material, in order, by way of example, to be able to measure a change in an optical property, for example a color change, on one or more test fields.

As an alternative or in addition to the abovementioned types of openings, test element openings can for example also be provided, preferably in turn for example at least one test element opening per chamber. Through these test element openings, one or more test elements can be introduced completely or in part into the chambers. As described in greater detail below, this can be effected for example in such a way that one or more test element fields are applied to said test element openings and/or introduced into said test element openings at least in part from outside in such a way that parts or regions of said test fields face the interior of the chambers. These regions, which are thus received inside the chambers, can thus form per se separate sub-aids in the form of test elements which can be assigned respectively to a chamber. This will be described in even greater detail below.

During the process of applying the at least one second component, it is possible, in particular, to secure the analytical aids in the chambers, in particular the receptacles of the first component, at least substantially against an unintentional change in position, in particular against slipping and/or rotating. This can be effected for example by a force and/or stress being exerted on the aids, which can be ensured for example by means of corresponding shaping of the first component and/or of the second component. Said force and/or stress and/or deformation may bring about for example a flexing of flexible aids, for example flexible lancets and/or microsamplers, in particular metal lancets in the form of flat lancets. The stress and/or force can for example be cancelled during a sampling movement and/or be overcome by the actuator, for example by the actuator providing a higher force and/or higher stress.

The method according to the invention can furthermore comprise a method step in which at least one test chemical is applied. Said test chemical can be applied for example to the first component and/or the second component and/or a third component, not yet mentioned, in particular a carrier. The process of applying the test chemical can be effected for example after the process of applying the second component, but can, as an alternative or in addition, also be effected in an upstream method step and/or simultaneously. As explained above, the test chemical is designed to change at least one measurable property in the presence of at least one analyte to be detected, for example an optically and/or electrically measurable property. In this regard, reference may be made in particular to the above description.

In this case, the process of applying the test chemical is effected in such a way that in each case at least one region of the test chemical faces the interiors of the chambers. By way of example, in each case one or a plurality of regions of the test chemical can be assigned to in each case exactly one chamber. This can be effected, for example, as explained above, by virtue of the fact that each chamber has, for example in its chamber wall, at least one test element opening to which the test chemical is applied from outside and/or into which the test chemical is introduced at least in part, such that in each case at least one region faces the interior of the respective chamber. In this way, from the regions of the test chemical which in each case face a chamber, in each case one or a plurality of test fields can arise which can be part of the analytical aid and which can form, in particular, one or a plurality of sub-aids of the analytical aids. In this case, the regions of the test chemical which face the interiors of the chambers are intended preferably to be accessible from inside the chambers.

The process of applying the at least one test chemical can be effected for example by means of at least one carrier. Thus, by way of example, a carrier in the form of one or more disks and/or films and/or other components and/or structural elements can be provided, to which the test chemical is applied and which is applied in such a way that the test chemical faces the chambers. The carrier can subsequently be removed and/or can also remain wholly or partly a constituent part of the analytical magazine.

After the test chemical has been applied, it can optionally additionally be covered, said test chemical being closed off and/or received in the analytical magazine in moisture-tight fashion, for example. In this way, by way of example, non-moisture-stable test chemicals can also be used. Particularly if moisture-stable test chemicals are used, however, such a covering of the test chemical can also be completely dispensed with.

It is possible to realize analytical magazines in which the chambers comprise analytical aids with at least one lancet and at least one test element in the form of at least one test field, for example. Thus, by way of example, by means of the at least one lancet and/or a collecting element or transfer element during a sampling movement, a sample of the body fluid can be produced and/or taken up and transferred inside the chamber. This transfer can be effected, as explained above, for example by means of a movement back as part of the sampling movement, wherein a part of the sample that has been taken up for example on the lancet and/or the collecting element and/or the transfer element is transferred inside the chamber. As an alternative or in addition, the taking up and/or the transfer, as explained above, can also be effected for example by a capillary action of at least one capillary element of the analytical aid, which performs a transfer inside the chamber currently being used in each case. The transfer can be configured, in particular, in such a way that during said transfer, the sample that has been taken up is transferred completely or partly to the at least one test element, in particular to one or more test fields, for example the above-described at least one test field produced by the process of applying the test chemical. For this purpose, the analytical system using the analytical magazine can also additionally comprise one or more actuators designed to support the transfer of the sample from the analytical aid, for example a lancet and/or a microsampler, to the at least one test element, for example a test field. By way of example, an actuator can be provided which engages into the chamber and presses a sample-laden lancet and/or a microsampler onto a test field.

The above-described method variant or variant of the test element magazine in which the test chemical is configured in such a way that at least one region of the test chemical faces the interiors of the chamber, in particular in the form of one or a plurality of test fields per chamber, can be carried out in particular in such a way that the test chemical is applied jointly for a plurality, preferably for all, of the chambers. Thus, by way of example, the at least one test chemical can be applied in the form of one or more test chemical fields, in particular in the form of one or more continuous test chemical fields. In this case, a test chemical field should be understood to mean an area coated with test chemical throughout or not throughout, which area can also comprise a plurality of non-contiguous sub-areas. This common test chemical field which is provided jointly for a plurality or preferably all of the chambers can be embodied for example in the form of a rectangular field, round field or field shaped in any desired manner, in principle. This test chemical field can be applied for example on the carrier described above, for example a carrier film and/or some other structural element. The carrier can comprise for example a plastic material, for example a plastic film, and/or a paper material and/or a ceramic material and/or a metallic material, or a combination of the stated and/or other materials. In particular, a continuous and preferably integral carrier can be used in this case.

In particular, the test chemical field, this being preferred particularly for round analytical magazines, can be configured in round or annular fashion. Thus, by way of example, at least one chemical ring can be provided which has an annular carrier, preferably a continuous and in particular integral carrier (for example a carrier ring), and also at least one test chemical field applied thereto, preferably a continuous test chemical field. As an alternative, however, provision may for example also be made of a differently designed test chemical disk and/or a test chemical tape, with a correspondingly designed carrier, preferably a continuous and/or integral carrier, and at least one test chemical field applied thereto. Other configurations are also possible, however, which can be adapted to the respective form of the analytical magazine. The test chemical field is intended to provide the regions of the test chemical for a plurality of chambers, preferably for all of the chambers simultaneously, in particular the test fields for the respective chambers. If a plurality of test fields with different test chemicals are provided per chamber, then it is possible, by way of example, for each type of test chemical, to provide or apply a separate test chemical field for a plurality or preferably all of the chambers. These different types of test chemical fields can be provided on separate carriers or else on common carriers. Preferably, a common carrier, in particular an integral carrier, is also provided in the case of a plurality of test chemical fields and/or a plurality of types of test chemical fields. In particular, the carrier can also be covered with the test chemical throughout, that is to say in such a way that the test chemical field is not interrupted for the individual chambers, but rather is formed integrally for the plurality of chambers, preferably for all of the chambers. As an alternative, however, it is also possible to use a carrier coated with test chemical not throughout. The carrier itself is preferably configured integrally itself, however, for example as an integral carrier ring.

As explained above, the method can comprise further method steps, in particular method steps in which the chambers are sealed completely or in part, individually, in groups or all together. For this purpose, in at least one further method step, at least one seal can be applied to at least one opening of the chambers. If a plurality of openings are provided per chamber, for example the openings mentioned above, then these can be closed off, or sealed, individually or in groups or jointly. In this case, the seal can for example also be applied in such a way that sealing is effected for each type of openings for a plurality or preferably all of the chambers simultaneously. In this case, sealing should generally be understood to mean a process of closing off the openings which, at least in the context of customary use durations or storage durations for the analytical magazine, at least substantially prevents ingress of ambient influences, in particular air humidity and/or germs, inside the chambers. In this way, by way of example, it is possible to ensure a constant quality of the analytical aids over a predetermined storage duration, for example a storage duration of a few months up to a few years.

The sealing can be effected for example by at least one sealing element, which is preferably configured in such a way that it does not impair the respective function or purpose of use of the respective at least one opening. By way of example, it is possible to configure the sealing in the case of the at least one sampling opening in such a way that the latter can be opened for the sampling movement by the analytical aid and/or a further element of the analytical magazine and/or of the analytical system, for example by piercing and/or by cutting. Accordingly, by way of example, the at least one actuator opening can be configured such that it is opened for an actuator movement in the context of the sampling movement, for example by the actuator itself and/or a further element of the analytical magazine and/or of the analytical system. If at least one measurement opening is provided, then the sealing of this measurement opening can be configured for example in such a way that the measurement opening is uncovered for a measurement. As an alternative or in addition, depending on the type of measurement, the sealing can also be configured for example in such a way that it enables an optical measurement, for example, for which purpose the sealing of the at least one measurement opening can be configured for example as transparent to detection light and/or excitation light.

The at least one optional test element opening can adopt a special role. This test element opening can be closed off and/or sealed for example as early as during the process of applying or by the process of applying the test chemical in accordance with the description above. In addition, at least one seal can be applied to this at least one test element opening, for example in order to seal remaining interspaces.

The seal can comprise one or more sealing elements, which can be adapted to the purposes described above and which can also be formed integrally for a plurality of openings. By way of example, corresponding sealing films can be provided, for example thin plastic films and/or metal films. Sealing elements of this type are known, in principle, from the prior art.

As explained above, an analytical magazine is furthermore proposed besides the proposed method in one or more of the method variants described. This analytical magazine may be producible for example according to a method in accordance with one or more of the method variants described, although other production methods can also be used, in principle. This analytical magazine comprises a plurality of analytical aids received in chambers. The analytical magazine furthermore comprises at least one test chemical which is designed to change at least one measurable property in the presence of at least one analyte to be detected.

Furthermore, it is proposed to realize the above-described aspect of jointly applying the test chemical for a plurality of chambers, preferably for all of the chambers, also if appropriate independently of the production method mentioned. Accordingly, the at least one test chemical can be applied to a continuous carrier and form at least in test chemical field within the meaning of the definition above. In particular, the at least one test chemical field and the continuous carrier can form at least one chemical ring and/or at least one test chemical tape. In this regard, reference may be made to the description above.

In this case, the test chemical field is applied to a continuous carrier. In this case, a continuous carrier should be understood to mean a carrier which carries test chemical for a plurality and preferably for all of the chambers simultaneously. In particular, the carrier can be configured in integral fashion, for example as a carrier ring. With regard to the possible configurations of the carrier, reference may be made for example to the above description of the method. This at least one test chemical field, which, as explained above, can have one or else a plurality of sub-fields, including non-contiguous sub-fields, here provides in each case at least one region of the test chemical field to the chambers, this in each case at least one region of the test chemical field facing the interiors of the chambers. As explained above, this at least one region can therefore produce in particular per chamber in each case at least one test field which forms a part of the analytical aids received in the chambers and/or of the sub-aids of said analytical aids.

The test chemical field can be in particular part of a housing of the analytical magazine, in particular part of an outer magazine housing wall. By way of example, as explained above, this can be effected by virtue of the fact that the test chemical field is applied to an opening of a housing part of the housing from outside, such that the test chemical field is accessible at least partly from inside the chamber. By way of example, as explained above, the housing can be formed in substantially rigid fashion, that is to say in such a way that it substantially does not change its form at least under the action of the forces resulting from its own weight. The housing can comprise for example the abovementioned components, that is to say the at least one first component, the optionally at least second component and, if appropriate, one or more further components. The housing can comprise for example one or more plastic materials and/or one or more ceramic materials and/or one or more further materials, for example thermoplastic materials, thermosetting plastic materials, if appropriate with corresponding fillers or combinations of the stated and/or other materials.

The described method and/or the described analytical magazine in one or more of the embodiments described has, as already indicated above, numerous advantages over known methods and devices. In particular, the analytical magazine can be used for so-called microsamplers, that is to say analytical systems in which the sample production and the sampling and optionally also the sample analysis are effected within a single integrated system. Preferably, it is possible in this case to take up small sample volumes, for example sample volumes of less than 1 µl, in particular less than 500 µl.

The production process can be substantially restricted to the handling of a small number of structural elements. In a first method step, by way of example, in accordance with one of the method variants described above, structures of individual lancets, for example needle elements, can be etched, for example from a metal sheet. In this way, it is possible for example to produce a metal disk comprising the holding element and the lancets. The individual lancets can be interconnected by means of the metal disk. The metal sheet can subsequently for example be laid into the first component, for example a plastic component of a housing produced completely or partly from plastic, and/or be laid onto the latter. During the subsequent separation of the lancets, the latter preferably directly in ordered fashion are deposited all at once into the chambers of the housing, preferably without separate orientation of the lancets being necessary for this purpose. In this way, by way of example, it is possible to dispense with handling of individual, in particular miniaturized, disposables during insertion into the respective magazine chambers. In a next step, the housing can be completed by a further housing part, the now separated lancets being held in their chambers, for example. Afterward, as explained above, the magazine housing can be covered with a chemical ring, for example, which preferably has a test chemical field throughout. Overall, the production costs and the outlay for production can be considerably reduced in this way.

Furthermore, by means of the method proposed, it is also possible to reliably prevent cross-contamination of the analytical aids within the chambers. By way of example, this can be achieved by one or more of the above-described connection methods by means of which a plurality of housing parts, for example the first component and the second component, are connected to one another, in which case, in particular, the individual chambers can be separated from one another. This can be effected by a laser welding method, in particular, wherein preferably adjacent chambers are separated from one another by continuous welding seams.

In particular the integral production of the analytical aids with the holding element or of sub-aids with the holding element has numerous advantages. Thus, by way of example, it is possible to use specific etching structures for the lancets and/or microsamplers, by means of which the lancets can be connected to the holding element, for example a metal sheet and/or metal frame. By way of example, as explained above, said etching structures can have desired breaking locations and/or tapered portions, such that, by way of example, when the individual lancets are broken out and/or separated in some other way from the holding element, there are no residual break-off residues that might impede sliding of the lancets within the chambers. A high process reliability can be ensured in this way.

As a result of the preferred rigid configuration of the test element magazine and/or the preferred process of jointly introducing the analytical aids into a plurality, preferably all, of the chambers by means of a corresponding holding element, it is also possible to achieve advantages for example over analytical aids connected by a tape or similar flexible elements and over the production of corresponding analytical magazines. Handling of tapes is not necessary in this case. Nevertheless, the rigid configuration is not absolutely necessary, however, since, by way of example, the magazine and/or the first component and/or the holding element can also be configured wholly or in part in flexible fashion, for example in the form of films, tapes, chains, or the like.

A second aspect of the present invention proposes an analytical magazine which, by way of example, but not necessarily, is producible according to the above-described method according to the invention. Therefore, for possible configurations of the analytical magazine described below, reference may be made to the above description of the method or of the analytical magazine producible by means of the method. However, other ways of producing the analytical magazine are also conceivable. In particular, the analytical magazine can also be produced in a different manner than by using a holding element for introducing the analytical aids. Furthermore, the analytical magazine can also be configured in a different manner than with a continuous test chemical, that is to say for example with separate test chemicals for each individual chamber. However, a common continuous test chemical field in which in each case at least one region faces a respective chamber, for example in the form of a test chemical ring, is particularly preferred in the context of the second aspect of the present invention as well. Furthermore, the above-described preferred configurations of the first aspect of the invention, as are in particular also presented in the dependent claims, can also be realized in the context of the second aspect of the invention as well, including independently of the other features of the first aspect of the invention.

The analytical magazine in accordance with the second aspect of the invention comprises a plurality of analytical aids. The analytical magazine has at least two chambers in which the analytical aids can be received. In this case, the analytical aids are received in at least one of the chambers. In this case, basically two principles for receiving in the chambers are conceivable. Thus, by way of example, in each case one analytical aid can be received per chamber, in particular an analytical aid which comprises at least one sub-aid in the form of a test element with a test chemical. Optionally, at least one further sub-aid in the form of a lancet and/or a microsampler can be provided, preferably in addition, per chamber. In the case of this principle, it is possible for the analytical aids to be remagazined in particular after use in the same chamber. As an alternative, however, remagazining in a different chamber is also possible. This first principle is preferred particularly in the case of disk-shaped or rod-shaped magazines. According to a further principle, at least one first chamber for unused analytical aids and at least one second chamber for used analytical aids can be provided. In this case, by way of example, the analytical aids can be removed from the first chamber for a use and be transferred into the second chamber after the use, which second chamber can be formed such that it is spatially separated from the first chamber. This principle can be used for example for tape magazines, wherein, by way of example, a good winding for receiving unused analytical aids is provided in a first chamber and a poor winding for receiving used analytical aids is provided in a second chamber.

The analytical aids comprise in each case at least one test element with at least one test chemical for detecting at least one analyte in a liquid sample, in particular a body fluid. In this case, the analytical aids are often also referred to as "tests", independently of the function and configuration thereof. In this case, therefore, a test can generally be understood to mean at least an analytical aid which can be utilized for a test process. By way of example, a test element or a lancet or else a pair comprising a test element and a lancet may be involved in this case, preferably exactly one test being mounted in exactly one chamber. A test can therefore comprise a plurality of associated sub-aids, for example. A test can be received in exactly one chamber, for example. In the context of the present invention, however, here and hereinafter no further distinction is made linguistically and in terms of contents between a test and an analytical aid, including the possibility that a test may comprise a plurality of sub-aids, for example in each case a test element and a lancet.

In conventional analytical magazines and test elements, in particular for detecting glucose, generally use is made of a test chemical which is sensitive to air humidity and whose function may deteriorate or even be lost entirely in the event of excessively long exposure to air. Accordingly, by way of example, conventional test strips have to be stored in containers that are moisture-tight with respect to air humidity. These containers are usually partly filled with a drying agent, that is to say a moisture-absorbing material, for example activated carbon. If, in the case of integrated systems, analytical magazines and/or analytical aids, for example disposable aids (disposables), are then developed in which test elements are packaged individually or in groups, these packagings also have to be made moisture-tight. However, this requirement for moisture-tightness extremely limits the choice of potential materials, in particular potential materials for the housing. This is owing to the fact that additional requirements may exist which have to be met at the same time. Thus, in most cases, the materials used have to be sterilizable, in particular by means of ionizing radiation. As an alternative or in addition, the materials used are generally not permitted to outgas, in particular not after or during exposure to radiation as a result of a sterilization process. Once again as an alternative or in addition, the materials used have to be suitable for the chosen production process, for example for an injection-molding method and/or some other shaping process. Once again as an alternative or in addition, the materials used should preferably be biocompatible and/or should be joinable and/or sealable. Further requirements may exist. In this case, in particular the requirement of moisture-tightness is a requirement that is difficult to satisfy in practice since most plastics are open to moisture in respect of diffusion, particularly in the case of small wall thicknesses, for example wall thicknesses of less than one millimeter.

According to the invention, therefore, the second aspect of the present invention proposes configuring the test chemical in this case in such a way that the latter is at least substantially stable with respect to ambient influences, in particular with respect to moisture. The test chemical can be present in particular as a dry chemical, in particular on a test strip. In the context of the present invention, a test chemical which is substantially stable with respect to ambient influences is understood to mean a test chemical which is stable with respect to air humidity and advantageously likewise with respect to sterilization methods, in particular sterilization methods using ionizing radiation. In this case, stable is the designation used if, during storage at 32° C. and a relative air humidity of 85% at standard pressure over a time duration of three weeks, the activity, for example the enzyme activity of the test chemical of the analytical aid, decreases by less than 50%, preferably by less than 30%, and particularly preferably by less than 20%. In this case, the activity can be determined in principle by means of any desired method known from the prior art since, in the context of the definition indicated, only a ratio of the decrease in the activity measured by this method to an activity measured by this method before storage or directly after the production of the analytical aid is of relevance. In this case, the activity can relate in particular to an enzyme activity of a dry chemical, in particular in a test strip. By way of example, methods are known which, for measuring the enzyme activity, extract the enzyme from the test chemical or the test strip and subsequently determine the activity by means of ultraviolet absorption, for example. In this regard, reference may be made for example to H. U. Bergmeyer: Methoden der enzymatischen Analyse [Methods of enzymatic analysis], Verlag Chemie, $2^{nd}$ edition 1970, page 417, or Banauch et al.: A glucose dehydrogenase for the determination of glucose concentrations in body fluids, Z. Klin. Chem. Klin. Biochem. 1975 March; 13(3): 101-7. By way of example, for the test, a test strip with the test chemical can be produced, the enzyme activity of an enzyme of the test chemical can be measured by means of a conventional method, then the above-described storage can be carried out and afterwards the same method for measuring the enzyme activity can be carried out again. This procedure is usually carried out with a representative collective of test strips or test chemicals. As an alternative or in addition to stability with respect to ambient influences in the form of air humidity, there may preferably also be high stability of the test chemical with respect to ambient influences in the form of radiation usually used for sterilizing the analytical aids and/or the analytical magazines overall, for example gamma radiation and/or beta radiation and/or some other type of ionizing radiation.

As an example of such a test chemical which is stable with respect to ambient influences, reference may be made to WO 2007/012494 A1 (see also US 2008/213809), already cited above. The test chemical presented therein can also be used in the context of the present invention, by itself or else in combination with one or more other test chemicals. As an alternative or in addition, the test chemical can also be configured in the manner described in EP 2093284 A1 or WO 2009/103540 (see also US 2011/0143416).

Thus, the test chemical can contain for example an enzyme and a stable coenzyme, which are stored together. It has surprisingly been found that long-term stabilization of several weeks or months at high relative moisture or even in liquid phase and at elevated temperatures is possible with the aid of a stable coenzyme. This perception is surprising because it is known that although enzymes have an increased short-term stability for some hours in the presence of native coenzyme, they show a lower stability over a longer period. Compared with these perceptions in relation to the prior art, it was surprising that an enzyme has a distinctly increased long-term stability in the presence of a stable coenzyme than does an enzyme in the presence of a native coenzyme, especially since the stable coenzymes have a lower binding constant with the enzyme than does the native coenzyme.

The enzyme stabilized by the method according to the invention may be in particular a coenzyme-dependent enzyme. Examples of suitable enzymes are dehydrogenases selected from a glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1), alpha-hydroxybutyrate dehydrogenase, sorbitol dehydrogenase or amino-acid dehydrogenase, e.g. L-amino-acid dehydrogenase (E.C.1.4.1.5). Further suitable enzymes are oxidases such as, for instance, glucose oxidase (E.C.1.1.3.4) or cholesterol oxidase (E.C.1.1.3.6) and amino transferases such as, for example, aspartate or alanine amino transferase, 5'-nucleotidase or creatine kinase. The enzyme is preferably glucose dehydrogenase.

It has proved to be particularly preferable to employ a mutated glucose dehydrogenase. The term "mutant" as used in the context of the present application refers to a genetically modified variant of a native enzyme which, while the number of amino acids is the same, has an amino acid sequence which is modified compared with the wild-type enzyme, i.e. differs in at least one amino acid from the wild-type enzyme. The introduction of the mutation(s) can take place site-specifically or non-site-specifically, preferably site-specifically by using recombinant methods known in the specialist sector, with at least one amino acid exchange within the amino acid sequence of the native enzyme resulting, appropriate for the particular requirements and conditions. The mutant particularly preferably has an increased thermal or hydrolytic stability compared with the wild-type enzyme.

The mutated glucose dehydrogenase can in principle comprise the amino acid(s) which is (are) modified by comparison with the corresponding wild-type glucose dehydrogenase at any position in its amino acid sequence. The mutated glucose dehydrogenase preferably includes a mutation at least one of positions 96, 170 and 252 of the amino acid sequence of the wild-type glucose dehydrogenase, with particular preference for mutants with mutations at position 96 and position 170, and mutations at position 170 and position 252. It has proved advantageous for the mutated glucose dehydrogenase to comprise no further mutations besides these mutations.

The mutation at positions 96, 170 and 252 can in principle include any amino acid exchange which leads to a stabilization, e.g. an increase in the thermal or hydrolytic stability, of the wild-type enzyme. The mutation at position 96 preferably includes an amino acid exchange of glutamic acid for glycine, whereas in relation to position 170 an amino acid exchange of glutamic acid for arginine or lysine, in particular an amino acid exchange of glutamic acid for lysine, is preferred. In relation to the mutation at position 252, this preferably includes an amino acid exchange of lysine for leucine.

The mutated glucose dehydrogenase can be obtained by mutation of a wild-type glucose dehydrogenase derived from any biological source, where the term "biological source" includes in the context of this invention both prokaryotes such as, for example, bacteria, and eukaryotes such as, for example, mammals and other animals. The wild-type glucose dehydrogenase is preferably derived from a bacterium, with particular preference for a glucose dehydrogenase from *Bacillus megaterium, Bacillus subtilis* or *Bacillus thuringiensis*, especially from *Bacillus subtilis*.

In a particularly preferred embodiment of the present invention, the mutated glucose dehydrogenase is a glucose dehydrogenase obtained by mutation of wild-type glucose dehydrogenase from *Bacillus subtilis*, which has the amino acid sequence depicted in SEQ ID No.: 1 (GlucDH_E96G_E170K) or that depicted in SEQ ID No.: 2 (GlucDH_E170K_K252L).

The stable coenzyme is preferably a coenzyme which has been chemically modified by comparison with the native coenzyme and which has a higher stability than the native coenzyme (e.g. hydrolytic stability). The stable coenzyme is preferably stable to hydrolysis under test conditions. Compared with the native coenzyme, the stable coenzyme may have a reduced binding constant for the enzyme, for example a binding constant reduced by a factor of 2 or more.

Preferred examples of stable coenzymes are stable derivatives of nicotinamide adenine dinucleotide (NAD/NADH) or nicotinamide adenine dinucleotide phosphate (NADP/NADPH), or truncated NAD derivatives, e.g. without the AMP moiety or with non-nucleoside residues, e.g. hydrophobic residues. Likewise preferred as stable coenzyme in the context of the present invention is the compound of the formula (I)

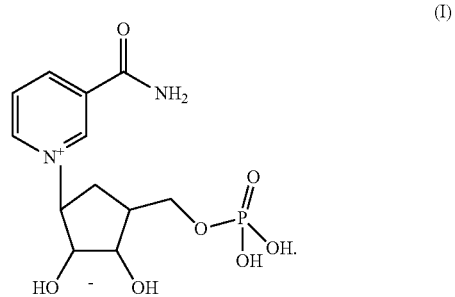 [SMILES: NC(=O)c1ccc[n+](C2CC(COP(=O)(O)O)C(O)C2O)c1]

Preferred stable derivatives of NAD/NADH and NADP/NADPH are described in the aforementioned references, the disclosure of which is hereby expressly incorporated by reference. Particularly preferred stabilized coenzymes are described in WO 2007/012494 (see also, US 2008/213809) and U.S. Pat. No. 7,553,615, the disclosure of which is hereby expressly incorporated by reference. The stable coenzyme is particularly preferably selected from compounds having the general formula (II)

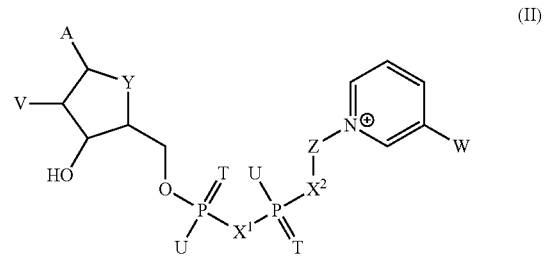

with

A=adenine or an analog thereof,

T=in each case independently O, S,

U=in each case independently OH, SH, $BH_3^-$, $BCNH_2^-$,

V=in each case independently OH or a phosphate group, or two groups forming a cyclic phosphate group;

W=COOR, $CON(R)_2$, COR, $CSN(R)_2$ with R=in each case independently H or $C_1$-$C_2$-alkyl, $X^1$, $X^2$=in each case independently O, $CH_2$, $CHCH_3$, $C(CH_3)_2$, NH, $NCH_3$,

Y=NH, S, O, $CH_2$,

Z=a linear or cyclic organic radical, with the proviso that Z and the pyridine residue are not linked by a glycosidic linkage, or a salt or, where appropriate, a reduced form thereof.

Z in the compounds of the formula (II) is preferably a linear radical having 4-6 C atoms, preferably 4 C atoms, in which 1 or 2 C atoms are optionally replaced by one or more heteroatoms selected from O, S and N, or a radical including a cyclic group which has 5 or 6 C atoms and which optionally comprises a heteroatom selected from O, S and N and optionally one or more substituents, and a radical $CR^4_2$, where $CR^4_2$ is bonded to the cyclic group and to $X^2$, with $R^4$=in each case independently H, F, Cl, $CH_3$.

Z is particularly preferably a saturated or unsaturated carbocyclic or heterocyclic 5-membered ring, in particular a compound of the general formula (III)

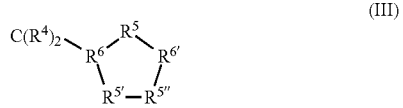
(III)

where a single or double bond may be present between $R^{5'}$ and $R^{5''}$, with
$R^4$=in each case independently H, F, Cl, $CH_3$,
$R^5=CR^4_2$,
where $R^{5'}$=O, S, NH, $NC_1$-$C_2$-alkyl, $CR^4_2$, CHOH, $CHOCH_3$, and
$R^{5''}=CR^4_2$, CHOH, $CHOCH_3$ if there is a single bond between $R^{5'}$ and $R^{5''}$, and
where $R^{5'}=R^{5''}=CR^4$ if there is a double bond between $R^{5'}$ and $R^{5''}$, and
$R^6$, $R^{6'}$=in each case independently CH or $CCH_3$.

In a preferred embodiment, the compounds according to the invention comprise adenine or adenine analogs such as, for example, $C_8$- and $N_6$-substituted adenine, deaza variants such as 7-deaza, aza variants such as 8-aza or combinations such as 7-deaza or 8-aza or carbocyclic analogs such as formycin, it being possible for the 7-deaza variants to be substituted in position 7 by halogen, $C_1$-$C_6$-alkynyl, -alkenyl or -alkyl.

In a further preferred embodiment, the compounds comprise adenosine analogs which, instead of ribose, comprise for example 2-methoxydeoxyribose, 2'-fluorodeoxyribose, hexitol, altritol or polycyclic analogs such as bicyclo-, LNA- and tricyclo-sugars.

It is possible in particular in the compounds of the formula (II) also for (di)phosphate oxygens to be replaced isotronically, such as, for example, $O^-$ by $S^-$ or $BH_3^-$, O by NH, $NCH_3$ or $CH_2$ and =O by =S.

W in the compounds of the formula (II) according to the invention is preferably $CONH_2$ or $COCH_3$.

$R^5$ in the groups of the formula (III) is preferably $CH_2$. It is further preferred for $R^{5'}$ to be selected from $CH_2$, CHOH and NH. In a particularly preferred embodiment, $R^{5'}$ and $R^{5''}$ are each CHOH. In yet a further preferred embodiment, $R^{5'}$ is NH and $R^{5''}$ is $CH_2$.

In the most preferred embodiment, the stable coenzyme is carbaNAD.

The preferred test chemical is configured in particular for long-term stabilization of the enzymes contained in it. This means that the enzyme stabilized with a stable coenzyme is stored, e.g. as dry substance, for example over a period of at least two weeks, preferably of at least four weeks and particularly preferably of at least eight weeks, and in this case the enzyme activity declines preferably by less than 50%, particularly preferably less than 30% and most preferably by less than 20% in relation to the initial enzyme activity.

The test chemical can further be configured for storage of the enzyme stabilized with a stable coenzyme at elevated temperatures, for example at a temperature of at least 20° C., preferably of at least 25° C., and particularly preferably of at least 30° C. The enzyme activity in this case declines preferably by less than 50%, particularly preferably less than 30% and most preferably less than 20% in relation to its initial level.

It is possible by the stabilization according to the invention for the enzyme stabilized with a stable coenzyme to be stored even without a drying reagent for a long time, as indicated above, and/or at high temperatures, as indicated above. It is further possible for the stabilized enzyme also to be stored at a high relative air humidity, e.g. a relative air humidity of at least 50%, in which case the enzyme activity declines preferably by less than 50%, particularly preferably less than 30% and most preferably less than 20% in relation to the initial level.

The storage of the enzyme stabilized with a stable coenzyme can take place on the one hand as dry substance and on the other hand in liquid phase. The storage of the stabilized enzyme preferably takes place on or in a test element suitable for determining an analyte. The enzyme stabilized with a stable coenzyme is in this case a constituent of the preferred test chemical which may where appropriate also comprise further constituents such as, for example, salts, buffers, etc. The test chemical is in this case preferably free of a mediator.

The enzyme stabilized with a stable coenzyme can generally be employed for detecting analytes, for example parameters in body fluids such as, for instance, blood, serum, plasma or urine, or in sewage samples or food products.

Analytes which can be determined are any biological or chemical substances which can be detected by a redox reaction, e.g. substances which are substrates of a coenzyme-dependent enzyme or are themselves coenzyme-dependent enzymes. Preferred examples of analytes are glucose, lactic acid, malic acid, glycerol, alcohol, cholesterol, triglycerides, ascorbic acid, cysteine, glutathione, peptides, urea, ammonium, salicylate, pyruvate, 5'-nucleotidase, creatine kinase (CK), lactate dehydrogenase (LDH), carbon dioxide etc. The analyte is preferably glucose. The detection of glucose with the aid of glucose dehydrogenase (GlucDH) is particularly preferred in this connection.

The alteration in the stable coenzyme by reaction with the analyte can in principle be detected in any way. It is possible in principle to employ here all methods known from the prior art for detecting enzymatic reactions. However, the alteration in the coenzyme is preferably detected by optical methods. Optical detection methods include for example the measurement of absorption, fluorescence, circular dichroism (CD), optical rotatory dispersion (ORD), refractometry etc.

An optical detection method which is preferably used in the context of the present application is photometry. Photometric measurement of an alteration in the coenzyme as a result of reaction with the analyte requires, however, the additional presence of at least one mediator which increases the reactivity of the reduced coenzyme and makes it possible for electrons to be transferred to a suitable optical indicator or an optical indicator system.

Mediators suitable for the purposes of the present invention are inter alia nitrosoanilines such as, for example, [(4-nitrosophenyl)imino]dimethanol hydro-chloride, quinones such as, for example, phenanthrenequinones, phenanthrolinequinones or benzo[h]quinolinequinones, phenazines such as, for example, 1-(3-carboxypropoxy)-5-ethyl-phenazinium trifluoromethanesulfonate, or/and diaphorase (EC 1.6.99.2). Preferred examples of phenanthrolinequinones include 1,10-phenanthroline-5,6-quinones, 1,7-phenanthroline-5,6-quinones, 4,7-phenanthroline-5,6-quinones, and the N-alkylated and N,N'-dialkylated salts thereof, with preference as counterion in the case of N-alkylated and N,N'-dialkylated salts for halides, trifluoromethanesulfonate or other anions which increase the solubility.

It is possible to use as optical indicator or as optical indicator system any substance which is reducible and on reduction experiences a detectable change in its optical properties such as, for example, color, fluorescence, reflectance, transmission, polarization or/and refractive index.

Determination of the presence or/and the amount of the analyte in the sample can take place with the unaided eye or/and by means of a detection device using a photometric method which appears to be suitable to a person skilled in the art. Heteropolyacids and in particular 2,18-phosphomolybdic acid are preferably used as optical indicators and are reduced to the corresponding heteropoly blue.

The alteration in the coenzyme is particularly preferably detected by measuring the fluorescence. Fluorescence measurement is highly sensitive and makes it possible to detect even low concentrations of the analyte in miniaturized systems.

An alternative possibility is also to detect the alteration in the coenzyme electrochemically using a suitable test element such as, for example, an electrochemical test strip. The precondition for this is once again the use of suitable mediators which can be converted by the reduced coenzyme, by transfer of electrons, into a reduced form. The analyte is determined by measuring the current which is needed to reoxidize the reduced mediator and which correlates with the concentration of the analyte in the sample. Examples of mediators which can be used for electrochemical measurements include in particular the aforementioned mediators employed for photometric measurements.

It is possible to use a liquid test to detect an analyte, in which case the reagent is for example in the form of a solution or suspension in an aqueous or nonaqueous liquid or as powder or lyophilizate. However, it is also possible to use a dry test, in which case the reagent is applied to a support, a test strip. The support may include for example a test strip including an absorbent or/and swellable material which is wetted by the sample liquid to be investigated.

A particularly preferred test format includes the use of the enzyme glucose dehydrogenase with a stable NAD derivative for detecting glucose, in which case a derivative of the reduced coenzyme NADH is formed. NADH is detected by optical methods, e.g. by photometric or fluorometric determination after UV excitation. A particularly preferred test system is described in US 2005/0214891, to which express reference is made here.

In particular, the stable test chemical can be configured to comprise an enzyme stabilized with a stable coenzyme, where the stabilized enzyme shows on storage for preferably at least two weeks, particularly preferably at least four weeks and most preferably at least eight weeks at a temperature of, preferably, at least 20° C., particularly preferably at least 25° C. and most preferably at least 30° C., where appropriate with high air humidity and without a drying reagent, a decline in the enzymatic activity of less than 50%, preferably less than 30% and most preferably less than 20% compared with the initial level.

Other types of stable test chemicals can also be used alternatively or additionally, for example the test chemical described in WO 2007/012494 A1 (see also, US 2008/213809). In principle, the test chemical can be contained in a test element in any desired manner. The test chemical and/or the test element may be suitable for carrying out dry or liquid tests. By way of example, the test chemical can be applied on a suitable carrier material for this purpose, for example on a plastic and/or a ceramic material and/or a paper material.

When a test chemical which is at least substantially stable with respect to ambient influences is used, as in the manner provided by the second aspect of the present invention, it is possible to have recourse to better and more precise connection techniques for producing the housing and/or to a larger choice of materials. Accordingly, the second aspect of the present invention proposes configuring the analytical magazine in such a way that the latter has a housing with at least two components, for example two magazine halves. In this case, the two parts need not necessarily be configured identically. The housing, in particular the at least two parts together, can form the at least two chambers. It is particularly preferred for the at least two parts to be connected to one another by a method without using an adhesive. In particular, cohesive connection methods without an adhesive are appropriate here. The use of at least one laser welding method is particularly preferred on account of the high precision and the low degree of contamination caused. Accordingly, the second aspect of the invention proposes connecting the at least two components to one another by means of a laser welding method.

With a laser welding method it is possible to obtain uniform welding seams with a small width and high precision, where the method at the same time is thermally well controllable and localizable and can also be carried out practically without any contamination.

Particularly when a laser welding method is used, it is appropriate, as is likewise proposed according to the invention, if a first of the at least two components and a second of the at least two components have a different transparency. By way of example, a first of the at least two parts can be configured such that it is almost completely transparent, and a second of the at least two parts can be configured such that it is absorbent within the wavelength range used for the laser welding method. In this case, the at least two components can preferably comprise the same basic material, but in each case with a different absorption for light in the visible and/or infrared and/or ultraviolet spectral range. By way of example, the at least two parts can have a different absorption in a spectral range of between 500 and 1200 nm, in particular in a spectral range of 700 to 1100 nm or 700 to 1000 nm, in which conventional lasers used for the laser welding emit, for example semiconductor lasers and/or Nd:YAG lasers. In order to achieve a different transparency or absorption of the at least two components, a basic material of the components, which can also be identical for both components, can be colored differently, for example by the basic material (for example polycarbonate, PC) of one of the parts being admixed with a dye in order to reduce a transparency. By way of example, the two components could have, in said wavelength range, a difference in transparency of at least 5%, preferably of at least 20% and particularly preferably of at least 50% for the laser radiation used. In this case, a transparency is understood to mean a transmittance.

If a welding method is used for connecting the at least two parts, then the welding seams can have for example a width of at most 0.5 mm, in particular of at most 0.3 mm and particularly preferably of at most 0.2 mm. As will be explained below, this makes a considerable contribution to increasing the packing density. In particular, it once again advantageously becomes apparent here that the test chemical is at least substantially stable with respect to ambient influences since a transfer of moisture from one chamber into another chamber is largely irrelevant in this case.

Generally, a multiplicity of materials can be used for the housing, in particular for the at least two components of the housing, for example for the two magazine halves. In particular, thermoplastics can be used. One particular advantage of the use of a test chemical which is at least substantially stable with respect to ambient influences consists precisely in the fact that these plastics do not have to satisfy special requirements with regard to imperviousness to moisture. Accordingly, the choice and design of the plastics can be effected for example according to other criteria, for example according to processability in a specific shaping process, for example during injection molding. It is also possible to have recourse to cost-effective materials. By way of example, one or more of the following plastics can be used: PC (polycarbonate); ABS (acrylonitrile-butadiene-styrene); COC (cycloolefin copolymers); PMMA (polymethyl methacrylate); PS (polystyrene); PET (polyethylene terephthalate). These materials have advantages with regard to their processing properties and/or with regard to their costs, but can be used only poorly, in principle, if the requirement for vapor tightness also has to be met.

PC has for example a high resistance to ionizing radiation and a high transparency for a broad spectrum. It is a cost-effective mass-produced material which, however, has a comparatively high permeability to water vapor. However, since this permeability is largely irrelevant, in principle, in the context of the present invention, particularly when the stable test chemical is used, and since the processing properties of this material are particularly good in practice, this material is particularly preferred in the context of the present invention.

ABS can be processed very well and, in particular, can be injection-molded very well, such that the use of this material is also advantageous. This material, too, has a comparatively good transparency for a broad light spectrum and also low costs.

COC admittedly has a high transparency in a broad spectral range from ultraviolet light through to the infrared spectral range and provides a good vapor barrier, but is comparatively expensive and only moderately stable with respect to ionizing radiation.

PMMA has only little or no intrinsic fluorescence at all in the ultraviolet spectral range and also has a good transparency for a broad light spectrum. The high vapor permeability of this material is tolerable in the context of the present invention, particularly when the stable test chemical is used, and it is a cost-effective material. Therefore, this material, too, can be used advantageously in the context of the present invention.

PS can be processed well, in particular by an injection-molding method. It has a good transparency for a broad light spectrum. Moreover, it is a cost-effective mass-produced plastic. Overall, therefore, this material, too, can be used successfully in the context of the present invention.

With this extended choice of materials that is no longer restricted by the requirement for vapor impermeability, it is possible, in principle, for the preferably at least two parts of the housing of the analytical magazine to be connected by means of laser welding, instead of a conventional one of ultrasonic welding and/or an adhesive-bonding method, which would be left for non-transparent materials. Identical materials can be welded in a very simple manner for example by means of a laser, for example PC to PC and/or COC to COC, etc., particularly if one part is light-absorbent for the laser wavelength, for example by means of corresponding coloration and/or doping, and the other part is configured such that it is transparent or more transparent. Although opaque parts can, in principle, also be irradiated in such a way that welding is possible, the welding seams then generally become coarser and need more space. By contrast when the parts to be connected to one another have high transparency and smooth surfaces, it is possible to obtain very narrow welding seams, for example welding seams having the abovementioned width of 0.3 mm. These small welding seams allow the analytical magazine to be made very small, for example with the preferred packing densities described above. Furthermore, in the case of laser welding it is possible to avoid the formation of dust, which usually occurs in other welding methods, for example in ultrasonic welding. Such formation of dust can become apparent in a negative way particularly in the case of analytical aids or sub-aids in the form of test elements since a test chemical of the test elements can be contaminated by dust and other contaminants which can occur during welding. If, as an alternative or in addition, lancets and/or microsamplers are used as analytical aids or as analytical sub-aids, then that likewise makes formation of dust apparent in a very negative way since, by way of example, hydrophilicity of the lancets and/or microsamplers can be influenced by the dust. This can be avoided by the use of the laser welding method. Furthermore, vibrations that might result in resonance of structures or parts of the analytical magazine do not occur. Moreover, no additional materials are required either, such as adhesives, for example, which might contaminate the interior of the chambers and/or the analytical aids, thereby jeopardizing hydrophilicity of lancets or microsamplers, for example.

Moreover, in particular by using laser welding and/or the preferred plastics, new methods become possible for closing off and/or sealing the analytical magazine, for example for sealing a finished analytical magazine. Hitherto, in many cases analytical magazines have been closed off thermally using films capable of being bonded by hot melt adhesives. However, the hot melt adhesives used in this case can influence the analytical aids, under certain circumstances. Thus, by way of example, vapors of the hot melt adhesive can influence lancets and/or microsamplers, for example can impair the hydrophilicity thereof. By means of the proposed invention, in particular using the laser welding method and/or the materials proposed, however, it is possible to use, as an alternative or in addition to, for example, metal films, e.g. aluminum films, for sealing the analytical magazine, one or more plastic films which, by way of example, can be welded by means of a laser instead of being adhesively bonded.

Overall, the newly acquired freedom with regard to the choice of materials thus affords a basis for a considerably more compact system. This is not only because the analytical magazine can be configured with a considerably smaller structural space and/or a considerably higher packing density. The analytical magazine can also be simplified greatly in terms of its production and/or its handling and be made more cost-effective.

The analytical magazine has in general, in particular in the second aspect of the present invention, preferably one or more of the following properties: a total volume of not more than 10 $cm^3$; an external radius of not more than 5 cm; an internal radius of between 0.5 cm and 2 cm; a thickness of not more than 1 cm; a number of analytical aids of 10 to 100; a volume of between 3 $cm^3$ and 30 $cm^3$; a packing density of the analytical aids of more than 5/$cm^3$.

It is particularly preferred if an external volume of the analytical magazine, that is to say a volume without taking account of holes or other openings in the analytical magazine, does not exceed 5 $cm^3$, preferably 3 $cm^3$ and particularly preferably 2 $cm^3$. By way of example, the external volume can be 1.94 $cm^3$. It is particularly preferred if an empty volume of the analytical magazine, that is to say a total volume of openings optionally present in the analytical magazine, does not exceed 0.8 $cm^3$, preferably 0.5 $cm^3$ and particularly preferably 0.4 $cm^3$. By way of example, the empty volume can be 0.39 $cm^3$. The openings can be for example inner openings of a disk-shaped analytical magazine into which, by way of example, a drive can engage. Said empty volume is not intended to encompass the interior space inside the housing, for example the chambers. In this case, a net volume is understood, in the context of the present invention, generally to mean the external volume minus the empty volume. Consequently, in the case of a circular-disk-shaped magazine, a volume results which essentially results from the diameter and the height of the circular disk, and, in the case of an annular-disk-shaped magazine, a net volume results which results in relation to the net volume of a corresponding circular disk by subtracting the volume of a central cutout. Accordingly, it is preferred if the net volume of the analytical magazine, that is to say the external volume minus the empty volume, does not exceed 5 cm$^3$ particularly preferably 3 cm$^3$, and in particular does not exceed 2 cm$^3$. By way of example, the net volume can be 1.55 cm$^3$.

In the context of the present invention, a packing density is generally understood to mean a number of analytical aids per net volume of the analytical magazine. As explained above, however, each analytical aid can comprise a plurality of sub-aids which can interact with one another, for example in each case as a test. Preferably, each analytical aid comprises as sub-aid a test element with at least one test chemical. In addition, each analytical aid can then comprise as further sub-aid at least one lancet which serves for the sample generation of a sample of body fluid, which is then applied to the associated test element. If an analytical aid contains a plurality of analytical sub-aids, then associated analytical sub-aids still count as an analytical aid, however, for the calculation of the packing density, for example by a test element and an associated lancet being counted as a common analytical aid. By way of example, in each case exactly one analytical aid with at least one test element and optionally at least one lancet can be received in a respective chamber. As explained above, however, other configurations are also possible.

Thus, the analytical magazine can be configured as an annular disk, for example, having an external diameter of less than 100 mm, for example 50 mm, and an internal diameter of a cutout of the annular disk of less than 50 mm, for example 22.5 mm. The analytical magazine can have for example a thickness of less than 5.0 mm, for example a thickness of 3.1 mm. The analytical magazine can preferably comprise more than 20 analytical aids, for example at least 50 analytical aids and even 100 analytical aids or more. By way of example, 50 analytical aids each having a test element and optionally each additionally having a lancet can be provided, where in each case a test element and an associated lancet count as an analytical aid, also called "test". By way of example, in each case one analytical aid of this type can be received in a respective chamber. Accordingly, the packing density can be for example at least 50 analytical aids/5 cm$^3$=1 analytical aid/0.1 cm$^3$, preferably at least 50 analytical aids/3 cm$^3$=1 analytical aid/0.06 cm$^3$ and particularly preferably at least 50 analytical aids/2 cm$^3$=1 analytical aid/0.04 cm$^3$. By way of example, the packing density can be 50 analytical aids/1.55 cm$^3$=1 analytical aid/0.031 cm$^3$. A different configuration of the analytical magazine as a configuration as a circular disk is also possible, however, for example with one or more of the geometries described above. A configuration as a tape magazine is also possible, for example, in which case, for example, one chamber of the tape magazine comprises a good winding with analytical aids that have not yet been used, and another chamber of the tape magazine comprises a poor winding, on which analytical aids that have already been used can be received.

High packing densities can also be achieved, in particular, by virtue of the fact that the analytical aids are mounted very close together, without a hermetic separation between the analytical aids having to be effected. In this regard, the use of the stable test chemical becomes apparent in a particularly advantageous way. Thus, by way of example, it is possible to use analytical magazines which have a housing having a wall thickness of at most 1.2 mm. In this case, a wall thickness should be understood to mean a thickness of the housing between a chamber comprising an analytical aid and the surroundings or an adjacent chamber, in particular at a thinnest location of the housing. It is particularly preferred if the wall thickness is not more than 1.0 mm, and in particular not more than 0.8 mm. By way of example, the wall thickness of from 0.3 mm to 0.8 mm can be chosen.

Once again as an alternative or in addition, the use of a drying agent such as activated carbon, for example, can be dispensed with in the analytical magazine. Accordingly, it is particularly preferred if the analytical magazine is configured in a manner free of drying agent. In this way, too, structural space can be saved.

If such a stable test chemical is used, then a moisture-impermeable configuration of the separation of the individual chambers can also be completely dispensed with, in principle. The analytical magazine can therefore generally comprise a plurality of analytical aids which are received in at least two chambers. In this case, the analytical aids can in turn each comprise at least one test element with at least one test chemical for detecting at least one analyte in a liquid sample, in particular a body fluid, wherein the test chemical is configured in such a way that it is at least substantially stable with respect to ambient influences, in particular with respect to moisture. In this case, in general in the second aspect of the invention, but also in the first aspect described above, the chambers can be configured such that they are separated from one another in such a way that moisture can be exchanged between the chambers, for example between adjacent chambers. By way of example, the chambers can have chamber walls, wherein gaps or other openings are provided in or alongside the chamber walls, preferably with an opening width of not more than 20 μm, in particular of not more than 10 μm. These opening widths on the one hand enable air humidity to be exchanged between the chambers, but generally hold back coarser contaminants or germs.

The analytical magazine in one or more of the configurations described above can additionally be advantageously refined in various ways. In particular, as explained above, an analytical aid can comprise in each case a test element with a test chemical, in particular the test chemical which is stable with respect to ambient influences, and a lancet. These sub-aids can be stored jointly in one and the same chamber, for example in each case a pair comprising a lancet and a test element in one chamber, or a plurality of such pairs in a common chamber. The use of the test chemical which is stable with respect to ambient influences, in particular air humidity and/or beta radiation, enables a primary requirement for separate packaging of lancets and test elements to be obviated. Furthermore, the need to package the test chemical tightly against water vapor and/or to insert a drying agent into the chambers and/or the analytical magazine can also be obviated. As a result, new concepts become possible in particular for a combined analytical magazine with lancets and test elements. It is not necessary for the lancets and the test elements to be stored separately from one another. In addition, as will be explained in even greater detail below, other materials are possible for the magazine parts since it is no longer necessary simultaneously to satisfy the requirements for radiation stability and vapor tightness together.

Since a barrier between the analytical aids, in particular between lancets and test elements, can be dispensed with, a considerably more compact arrangement of lancet elements and test elements can be effected, for example in the same chamber of the analytical magazine. The lancet tip can lie closely alongside the test chemical in the case of storage in the chamber, for example, which, after a sample has been obtained, is also suitable as a position for transferring the sample to the test chemical. As a result, a mechanism for actuating the analytical aid can be designed considerably more simply than in the case of conventional analytical magazines since, by way of example, an additional movement for the purpose of overcoming a second barrier, as a barrier between lancet and test element, can be dispensed with and since it is not necessary to move to an additional position with the lancet. In contrast to previous concepts with separate packaging of lancet and test chemical, the test chemical also need not necessarily be moved in order to remove it from its packaging. In this case, generally it is only necessary for the lancet to be docked to a corresponding actuator and moved.

Accordingly, a further method for producing an analytical magazine is furthermore proposed in an additional aspect of the present invention. The analytical magazine can be, in particular, an analytical magazine in accordance with one or more of the configurations described above and/or an analytical magazine which can be produced in accordance with a method in accordance with one or more of the configurations described above. However, other configurations are also possible, in principle.

The analytical magazine is designed to receive a plurality of analytical aids in a plurality of chambers. The analytical aids each have at least one test chemical. In particular, this can be a test chemical which is at least substantially stable with respect to ambient influences in accordance with the above description. The test chemical can be for example part of test elements which are received preferably completely in the housing, for example in the chambers. In the method according to the invention, a plurality of analytical aids are introduced into at least one of the chambers. By way of example, exactly one analytical aid can be introduced per chamber, or a plurality of analytical aids can be introduced into one chamber. The analytical magazine furthermore has a housing with at least two components. The at least two components are connected to one another by a laser welding method before or after the process of introducing the analytical aids into the at least one chamber. The analytical aids can additionally have in each case at least one lancet. These lancets preferably have at least one capillary channel for taking up body fluid, which is passed to the test element via the lancet. Advantageously, such a capillary channel of the lancet (for example of a needle element), in particular a capillary structure, is coated, preferably hydrophilically coated, in order to enable improved transport of the body fluid. The analytical magazine can furthermore be sterilized using ionizing radiation, in particular after the laser welding method has been carried out. For the advantages of the proposed method in one or more of the configurations described, reference may largely be made to the description above. In particular, the laser welding method has the effect that a high packing density can be realized and that the analytical aids, in particular the lancets, during the production method, are not contaminated or are contaminated only to an insignificant extent, for example with dust that might deposit on the hydrophilic coating of the lancet.

DRAWINGS

Further details and features of the invention will become apparent from the following description of preferred exemplary embodiments. In this case, the respective features can be realized by themselves or as a plurality in combination with one another. The invention is not restricted to the exemplary embodiments. The exemplary embodiments are illustrated schematically in the figures. In this case, identical reference numerals in the individual figures designate identical or functionally identical elements, or elements which correspond to one another with regard to their function.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 6:
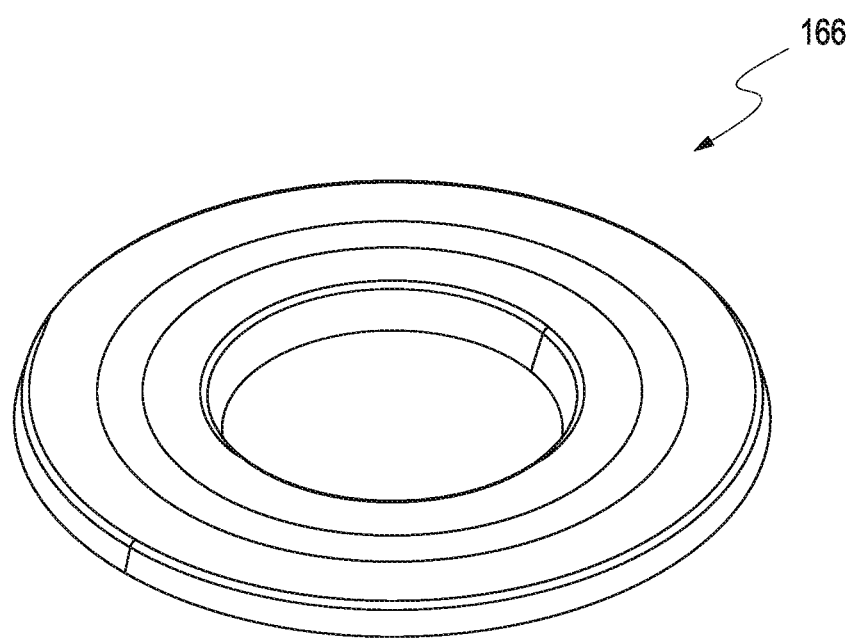
FIG. 6 shows an exemplary illustration of a sealing element for sealing openings of the analytical magazine.
Figure 7:
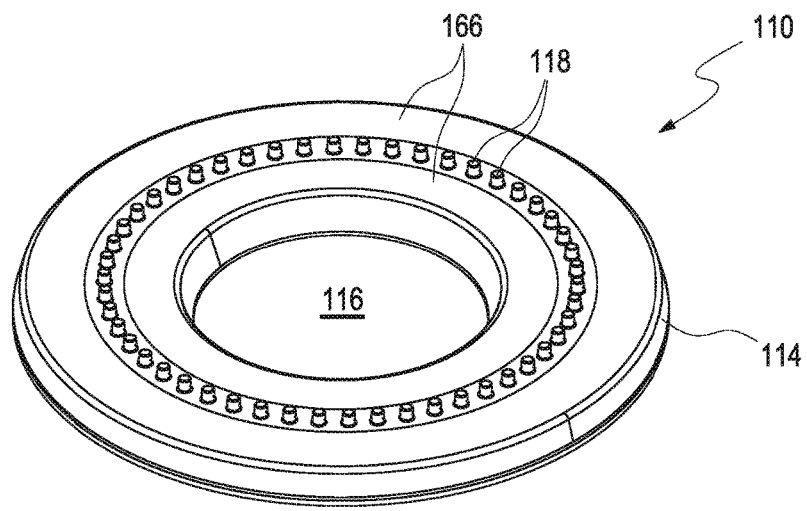
FIGS. 7A and 7B show different perspective illustrations of a finished analytical magazine.
Figure 7:
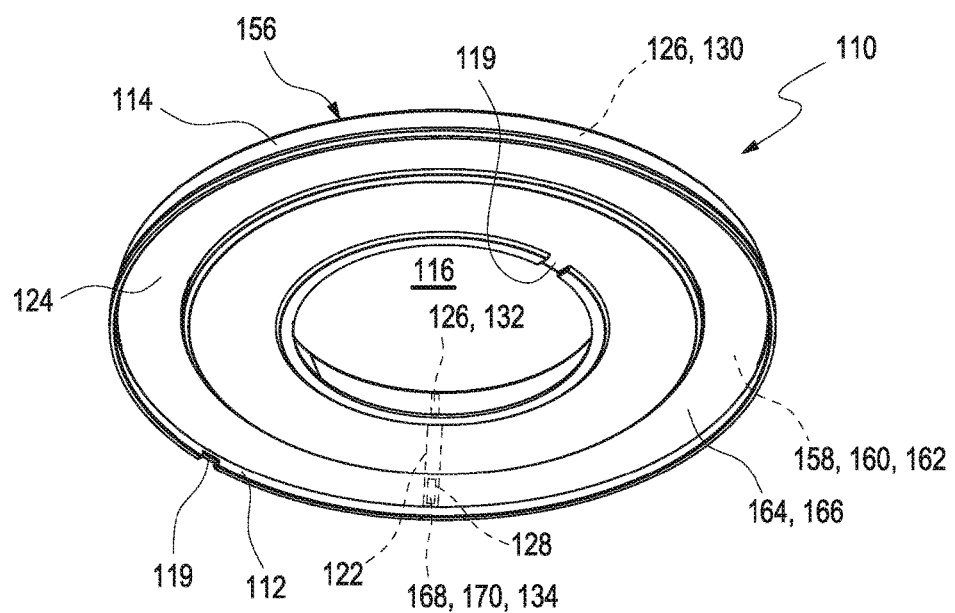

One possible embodiment of a method according to the invention for producing an analytical magazine 110 and also an exemplary embodiment of such an analytical magazine 110 are described below with reference to FIGS. 1A-7B. The finished analytical magazine 110 is illustrated in FIGS. 7A and 7B. In this case, the analytical magazine 110 constitutes an exemplary embodiment of the above-described first aspect of the invention, in which a plurality of analytical aids are introduced into a housing simultaneously during production. However, the analytical magazine can also function as an exemplary embodiment of the above-described second aspect of the invention, according to which a laser welding method is used as the connection technique.

Figure 1A:
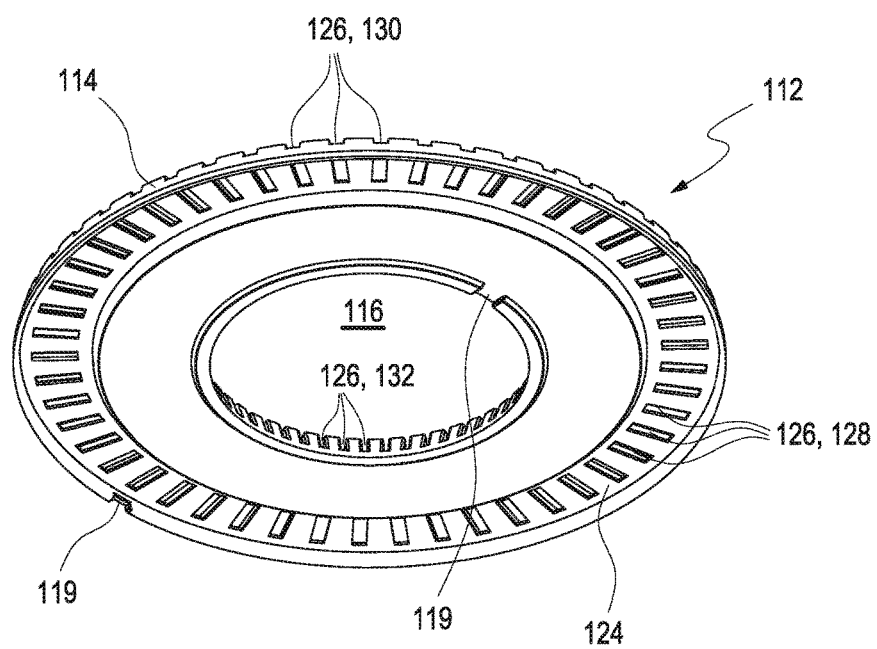
FIGS. 1A and 1B show different perspective illustrations of a first component of an analytical magazine.
Figure 1B:
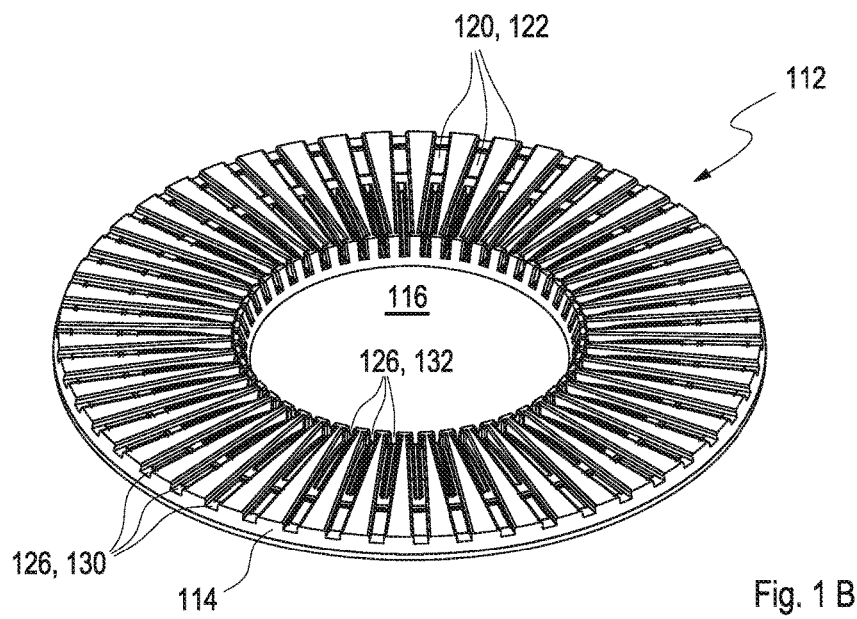
Figure 2:
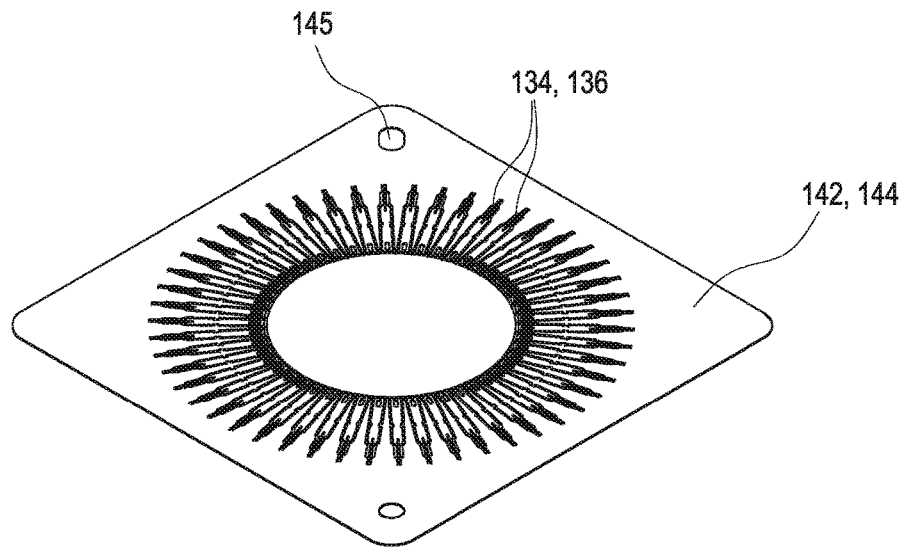
FIGS. 2A and 2B show provision of a plurality of analytical aids in the form of lancets.
Figure 2:
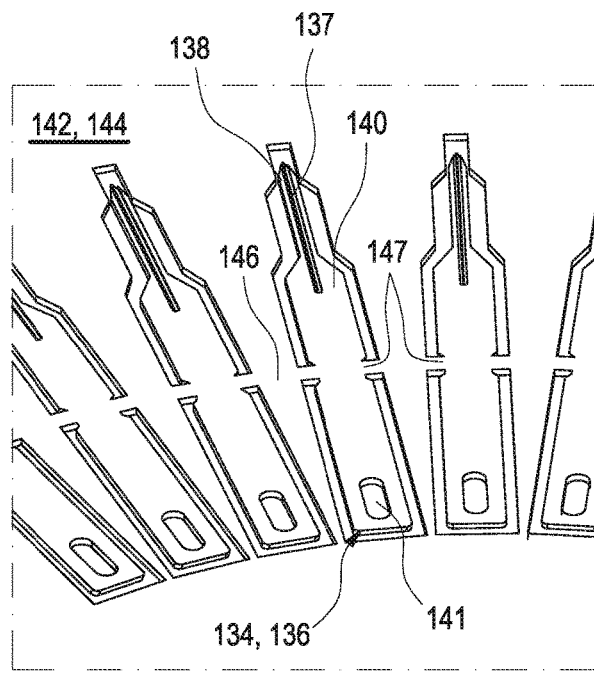

In a first method step, which is illustrated in FIGS. 1A and 1B, a first component 112 of the analytical magazine 110 is provided. In this case, FIG. 1A shows a view of the first component 112 from below, that is to say a perspective illustration obliquely from a side of the first component 112 which faces away from the interior of the analytical magazine 110, whereas FIG. 1B shows a perspective illustration obliquely from above, that is to say from a side which faces the interior of the analytical magazine 110 in the assembled state of the analytical magazine 110.

As can be discerned from the illustrations, the first component 112, as well as the analytical magazine 110 as a whole, is configured in the form of an annular disk, with an outer circumferential side 114 and a circular inner opening 116. An analytical system which uses the analytical magazine 110, said system not being illustrated in the figures, can, by way of example, receive the analytical magazine 110 completely or in part and can engage into the inner opening 116 completely or in part. Thus, by way of example, an actuator and/or a centering of the analytical system can engage into the toothing of the inner opening 116 completely or in part. The analytical system can have, by way of example, a corresponding transport device which interacts with transport elements 118 (see, for example, FIG. 5 below) on the analytical magazine 110, for example in order to bring about further transport, for example cyclic advance, of the analytical magazine 110. In this regard, reference may be made to the prior art, for example. The transport elements can comprise for example corresponding grooves, teeth, hooks, pins, projections, depressions or the like. The transport elements 118 are illustrated for example in FIG. 5, which is described in greater detail below, where they are configured in pin form by way of example. Furthermore, the analytical magazine 110 optionally comprises notches 119 in FIG. 1A. These notches 119 may serve for example for positioning in an assembly device, such as the outer one of the notches 119 in the example illustrated. In the example illustrated, the inner notch 119 serves for lowering a gate during production by means of a shaping method, for example an injection-molding method.

As illustrated in FIGS. 1A and 1B, the first component 112 can thus be configured for example as an annular disk and can be produced for example completely or partly from a plastic material. The first component 112 has a plurality of receptacles 120, which form parts of chambers 122 in the assembled state of the analytical magazine 110. These receptacles 120 and chambers 122 can be discerned in FIG. 1B. As can be seen from this illustration, the receptacles 120 in the exemplary embodiment illustrated are arranged radially and have corresponding depressions in the first component 112. The receptacles 120 are preferably just wide enough that a puncturing and collecting element, described in greater detail below, as an analytical aid and/or sub-aid, can just be mounted in said receptacles 120. Accordingly, by way of example, the outer dimensions of the receptacle 120 can correspond to said analytical aids, plus an amount of play, if appropriate, for example in each case a few hundreds of a millimeter in one or more dimensions, in the form of a gap, for example, which can ensure the mobility of the puncturing and collecting elements or analytical aids.

On the opposite side, that is to say on the side facing away from the receptacles 120, the first component 112 has an annular groove 124 in the exemplary embodiment illustrated. Openings 126 are respectively provided within said annular groove 124 in the exemplary embodiment illustrated, in each case one of said openings 126 being provided per chamber 122 in the exemplary embodiment illustrated. Said openings 126 are embodied in the form of elongate, radially extending slots in the exemplary embodiment illustrated. In the exemplary embodiment illustrated, said openings 126 subsequently serve as test element openings 128 or test field windows which respectively define a test field accessible from the chambers 122. This is explained in greater detail below.

Alongside the test element openings 128, the chambers 122 have further openings 126 in the exemplary embodiment illustrated. These openings 126 have in part already been formed in the first component 112, but can also be included wholly or in part in further components of the analytical magazine 110. Thus, the receptacles 120 in the exemplary embodiment illustrated, as can be seen from FIG. 1B, in particular, have openings 126 on the outer circumferential side 114, which openings subsequently serve as sampling openings 130. Through these sampling openings 130, the analytical aids can emerge completely or in part for a sampling movement. Furthermore, the receptacles 120 have openings 126 on the side facing the inner opening 116, which openings function as actuator openings 132 during subsequent operation of the analytical magazine 110 and enable an actuator (not illustrated) to enter inside the chambers 122, for example in a chamber 122 of the analytical magazine 110 which is currently situated in an application position.

In a further method step, illustrated in FIGS. 2A and 2B, a plurality of analytical aids 134 are provided. In the case illustrated, these are lancets 136 in the form of microsamplers which can form in each case an analytical aid 134 or a sub-aid of these analytical aids 134. In this case, FIG. 2A shows a perspective overall illustration of the lancets 136 provided, whereas FIG. 2B shows a detail illustration. In the exemplary embodiment illustrated, the lancets 136 are configured as microsamplers and have a tapered lancet end 138 facing outward with a lancet tip, and also a widened lancet body 140 in each case. At the opposite end with respect to the lancet tip, the lancets 136 can comprise one or more coupling elements 141 for coupling an actuator, for example an eye, a pilot hole or the like. Each lancet 136 has a capillary channel 137, for example a capillary gap, which is indicated by a dashed line in FIG. 2B and which serves for taking up a blood sample. The lancets 136 can be worked, for example etched, as flat lancets, from a metal disk 142, which can be discerned in FIG. 2A. The metal disk 142 can carry for example a single radial lancet arrangement or a plurality of lancet arrangements which, by way of example, can be applied successively into different magazine housings.

The metal disk 142 and/or parts of said metal disk 142 serve as a holding element 144, by means of which the lancets 136 are interconnected. Said holding element 144 can comprise an etching grid, for example, which was etched from the metal disk 142. The lancets 136 can be connected to the holding element 144 by connecting elements 146, which can be part of the holding element 144 or which can also directly form the holding element 144, for example by means of the lancets 136 being interconnected directly by means of webs or the like. The connecting elements 146 can act for example in tapered portions 147—which can be discerned in FIG. 2B—in the lancet body 140. The connecting elements can comprise desired braking locations, in particular, which enable the lancets 136 to be broken more easily from the assemblage illustrated in FIGS. 2A and 2B. The tapered portions 147 ensure that braking burrs are offset inward from the edge of the lancet body 140, such that these braking residues do not impede movement of the lancets 136 in the chambers 122.

Figure 3:
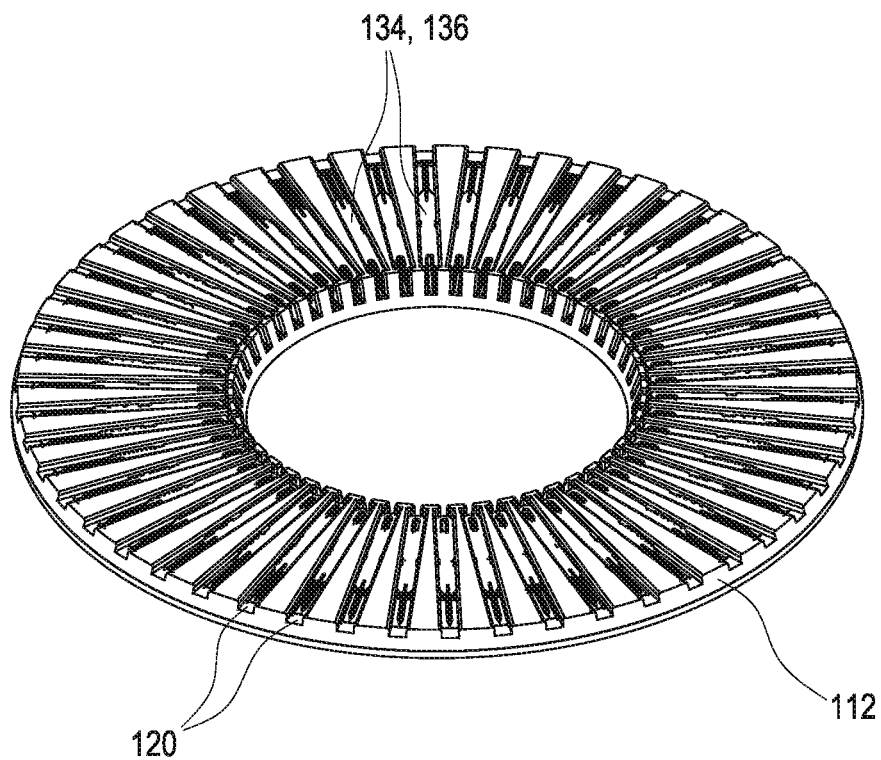
FIG. 3 shows the first component in accordance with FIGS. 1A and 1B after insertion of the lancets in accordance with FIGS. 2A and 2B.

The lancets 136 are provided in radial orientation by means of the holding element 144 in the case of the provision in FIGS. 2A and 2B, such that a lancet 136 is respectively oriented in a manner corresponding to the receptacles 120 in FIG. 1B. Afterward, the analytical aids 134 or lancets 136 connected to one another in this way are optionally separated from the holding element 144, for example by being broken out, and laid into the receptacles 120 of the first component 112 and separated from the holding element 144, for example by being broken out. The process of breaking out can be effected before and/or after the process of laying into the receptacles 120. The result of these method steps is illustrated in FIG. 3. The illustration here is analogous to FIG. 1B, and so reference may largely be made to said figure.

The process of laying the analytical aids 134 or lancets 136 into the receptacles 120 can be effected for example by the holding element 144 being gripped by means of a suction unit, a gripper or similar devices and being correspondingly positioned. This process can be effected automatically or else manually. The metal disk 142 and/or the holding element 144 can comprise further positioning aids for this purpose, for example the positioning openings 145 indicated in FIG. 2A. The analytical aids 134 or the connecting elements 146 can be separated for example by mechanical stamping, exertion of pressure or similar separating methods, for example the braking described above. In this case, the individual lancets 136 can be fixed for example on a separating tool, for example magnetically and/or by means of a vacuum fixing or a similar fixing device, in particular until the lancets 136 lie in their respective chambers 122.

This illustration reveals that one purpose of the receptacles 120 may consist in fixing the analytical aids 134 at least in part in terms of their spatial orientation after separation from the holding element 144. The receptacles 120 can be configured accordingly, in which case they need not necessarily comprise depressions, as illustrated in the figures, and so said depressions can for example also be replaced by other elements and/or be configured with a depth as small as desired, in principle. However, the embodiment illustrated is preferred on account of the good fixing, the depth of the receptacles 120 preferably being made at least equal to the depth of the lancets 136 or of the analytical aids 134.

The process of separating the analytical aids 134 can be effected before, during or after the process of inserting the analytical aids 134 into the receptacles 120. Thus, by way of example, a process of separating can be effected after the process of laying in and/or already while the analytical aids 134, still connected to one another by means of the holding element 134, are positioned in a manner hanging above the first component 112. The process of separating can be effected simultaneously in particular for all of the analytical aids 134 or for a plurality of analytical aids 134, such that, by way of example, all of the lancets 136 can be broken from the holding element 144 or the etching grid all at once, whereupon they can fall into the underlying receptacles 120.

Figure 4:
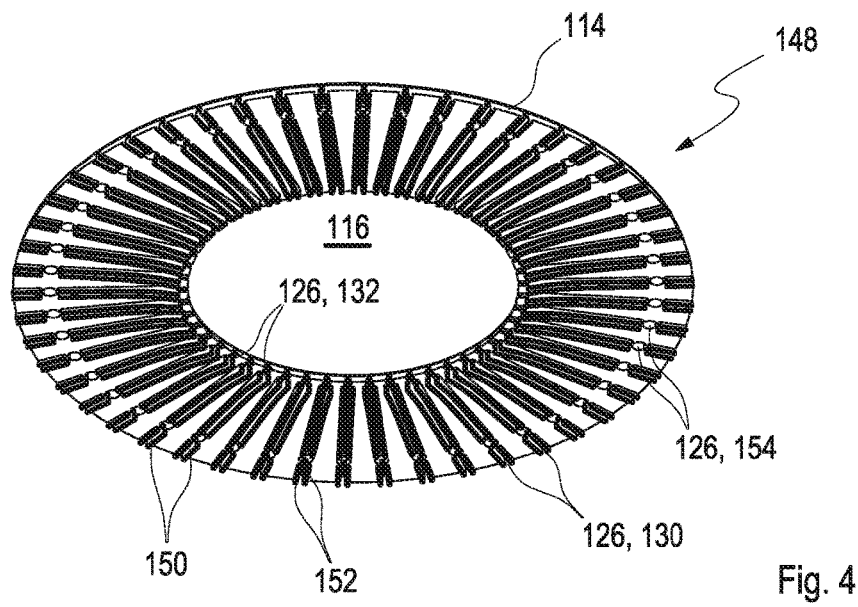
FIG. 4 shows a perspective illustration of a second component of the analytical magazine.

In a further method step, it is possible to close off the receptacles 120 with the analytical aids 134 received therein. This can be effected, in principle, by applying any desired second component 148, which, by way of example, can also be configured in the form of a film. In an optional case illustrated in FIG. 4, however, the second component 148 is configured for example as an annular disk which functions as an upper part. This annular disk, where FIG. 4 shows a view obliquely from below (that is to say a view from the chambers 122) of said second component 148, can for example likewise be produced from plastic and is preferably configured such that it is substantially rigid.

The second component 148 can comprise a plurality of elements corresponding to the receptacles 120. In the exemplary embodiment illustrated, the second component 148 comprises a plurality of depressions 150 which correspond to the receptacles 120 and which are likewise configured in radial fashion. By way of example, as indicated in FIG. 4, said depressions 150 can in turn comprise openings 126 on the outer circumferential side 114 and/or on the side facing the inner opening 116. Said openings 126 can subsequently form part of the sampling openings 130 and/or actuator openings 132.

Furthermore, the second component 148 comprises a plurality of ribs 152 which are likewise arranged in a manner corresponding to the receptacles 120. Said ribs can impose elastic bending on the analytical aids 134, for example the lancets 136 or samplers, if appropriate together with curved bottoms of the receptacles 120 of the first component 112, and in this way secure them against falling out.

Figure 5:
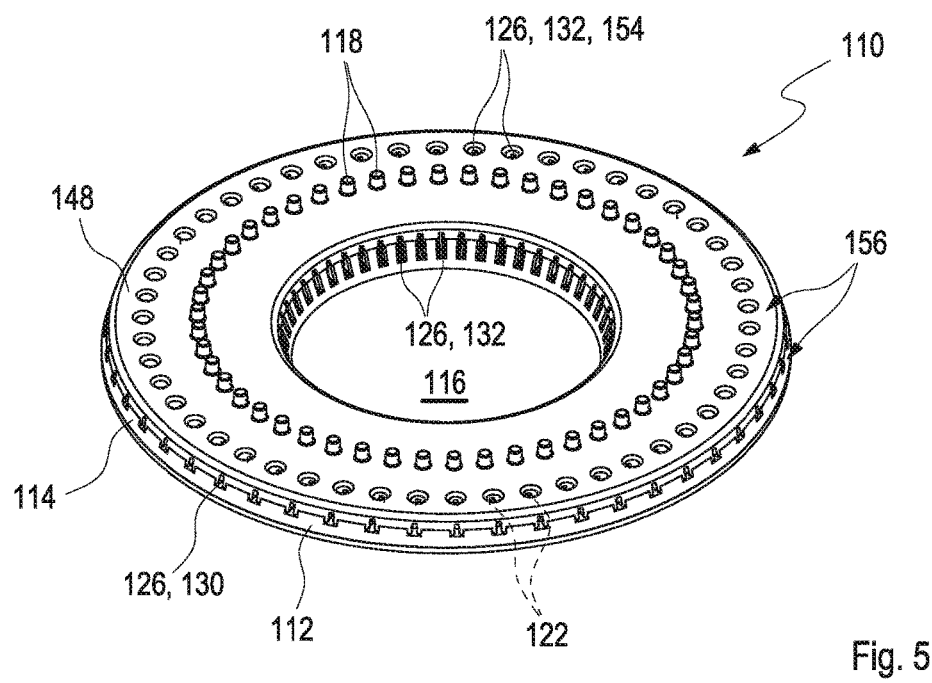
FIG. 5 shows a perspective illustration of the analytical magazine after application of the second component in accordance with FIG. 4.

FIG. 5 illustrates the analytical magazine 110 or a semi-finished part of said analytical magazine 110 after the second component 148 has been applied to the first component 112 shown in FIG. 3. A perspective illustration obliquely from above is shown here, with the view directed at the second component 148. The second component 148 and the first component 112 can be connected to one another, for example, in particular by means of a welding method, for example laser welding. For this purpose, by way of example, one of the components 112, 148 can be configured such that it is transparent to laser radiation, whereas the respective other of said components 112, 148 can be configured such that it is absorbent for the laser radiation. In particular, the two components 112, 148 can therefore be produced from materials having different absorption properties. The use of one or more of the plastics presented above is particularly preferred. In this case, for the two components 112, 148 it is possible to use identical basic materials, in principle, for example identical plastics, which differ in their absorption properties, however, for example through a mixture of additives such as dyes, for examples. In this way, in particular in a wavelength range of between 500 nm and 1200 nm, in particular between 700 nm and 1100 nm, it is possible to create a difference in an absorption of the components 112, 148 and/or of constituent parts of said components 112, 148, for example a difference in an absorption of at least 20%, preferably at least 50% or even at least 80% or more.

It can be discerned from the figures that the second component 148 can provide transport elements 118, for example, on its top side, which cannot be discerned in FIG. 4. Furthermore, this being discernible only with difficulty in FIG. 4, it is clearly discernible in FIG. 5 that the second component 148 provides a plurality of further openings 126 in the form of transfer openings 154. These transfer openings 154 can be configured for example in such a way that in each case one of said transfer openings 154 is provided per chamber 122. Accordingly, the transfer openings 154, which are illustrated as round transfer openings 154 in the exemplary embodiment illustrated, are arranged in circular fashion on the top side of a housing 156 of the test element magazine 110, said housing being formed by the first component 112 and the second component 148. However, other configurations are also possible, in principle.

The transfer openings 154 in the second component 148 subsequently serve, during the use of the analytical magazine 110, for example in an analytical system, to enable a sample to be transferred from a lancet 136 to a test field 170, which is described in greater detail below. Accordingly, for example an actuator, for example a plunger, can penetrate through a transfer opening 154 into a chamber 122, for example a chamber 122 situated in an application position of an analytical system, and press the sample-laden lancet 136 (or the microsampler) onto the test field 170, such that the sample is transferred from the lancet 136 to the test field 170. The transfer openings 154 can therefore also serve as actuator openings 132 and are correspondingly designated as such in the figures.

In a further method step, a test chemical 158 is then applied on the underside of the housing 156. This is indicated in FIG. 7B. Said test chemical 158 can be configured for example in the form of a test chemical field 160, in particular a continuous test chemical field 160, preferably in the form of a ring-shaped test chemical field 160. The test chemical 158 is preferably configured in such a way that it is at least substantially stable with respect to ambient influences, in particular with respect to air humidity. Stability with respect to conventional ionizing radiations used for sterilization is also advantageous. For possible configurations of the test chemical 158, reference may be made to the description above.

The test chemical 158 can be applied for example to a carrier 164, for example a likewise annular carrier 164, which is preferably configured as a continuous carrier 164 for all of the chambers 122, preferably as an integral carrier 164. The carrier 164 and the test chemical field 160 together form a continuous chemical ring 162 in this exemplary embodiment. By way of example, the carrier 164 can be configured in the form of a self-adhesive or non-adhesive film and/or a plastic carrier. Other carrier materials are also possible, in principle. Said carrier 164 with the test chemical 158, which is arranged on the top side of the carrier 164 in the illustration shown in FIG. 7B, is introduced into the annular groove 124 on the rear side of the first component 112 in the exemplary embodiment illustrated. The test element openings 128 are preferably completely closed off by the test chemical 158 and the carrier 164, such that the carrier 164 and/or the test chemical 158 can simultaneously also act as a seal 166 of the test element openings 128. As an alternative or in addition, however, an additional seal 166 can also be provided. The latter can be applied for example on the rear side of the carrier 164 after the application of the carrier 164 into the annular groove 124, for example by means of an adhesive-bonding method and/or laminating method.

The carrier 164 and/or the test chemical field 160 are preferably completely covered with the test chemical 158. In the regions in which the test chemical field 160 covers the test element openings 128, the regions 168 of the test chemical field 160 respectively form test fields 170 which face the interior of the chambers 122 and which therefore likewise form part of the analytical aids 134, or sub-aids.

The test chemical 158 then lies directly below the lancets 136 in the chambers 122, and each of the chambers 122 is separated from the next chamber 122. Only the sampling openings 130, the actuator openings 132 and the transfer openings 154 are still open. If a sampling movement is then carried out by means of the lancet 136, body fluid, in particular blood, can be taken up by the capillary channel 137, for example by means of a capillary effect, and/or a surface effect of the lancet 136. As a result of the lancet 136 moving back into the chamber 122, the body fluid then passes into the vicinity of the test chemical 158, such that the sample can be transferred from the lancet 136 to the test chemical 158 or the corresponding test field 170 of the chamber 122 currently being used.

In order that the chambers 122 that are not currently being used are protected against ambient influences, in particular moisture, the further openings 126 can be sealed in a method step which precedes, takes place in part at the same time as, or succeeds, the method step in FIG. 7. Thus, FIG. 6 illustrates by way of example a seal 166 which can be used in order, by way of example, to seal the measurement openings 154 and/or the actuator openings 132 and/or the sampling openings 130 simultaneously or successively. Said seal can comprise for example a round sheet composed of thin aluminum film or similar film-type elements. The seal 166, which can also be formed in multipartite fashion, can be preformed by means of a deep-drawing method, for example. The seal 166 can be connected to the housing 156 for example in a positively locking manner and/or cohesively and/or in a force-locking manner, for example by adhesive bonding and/or lamination.

In FIG. 7A, the analytical magazine 110 is finally illustrated in sealed form. As explained above, said analytical magazine can be laid for example into an analytical system in which the analytical magazine 110 can be rotated about an axis of rotation by means of a corresponding transport mechanism, for example, in order to move for example a respective one of the chambers 122 into at least one application position, for example for a sampling movement. Furthermore, further positions can be provided, for example measurement positions, in which a measurement of color changes and/or changes in other properties of the test fields 170 can be measured through the measurement openings 154, for example.

In the application position, on the inner circumference facing the inner opening 116, an actuator, for example an actuator comprising at least one actuating plunger, can engage, for example puncture, into the chamber 122 respectively situated in the application position, in which case (for example simultaneously and/or beforehand) the seal 166 of the actuator opening 132 of the chamber 122 situated in the application position can be opened, for example pierced. Through the seal 166, for example the film, on the outer circumferential side 114, the samplers in the form of the lancets 136 then emerge upon actuation.

A measurement of changes in the properties of the test fields 170 can be effected for example from an outer side of the analytical magazine 110, for example through the carrier 164 of the test chemical 158. For this purpose, the carrier 164 can be configured for example such that it is wholly or partly transparent, such that, by way of example, in FIG. 7B, a measurement of color changes can be effected from the underside of the test element magazine 110.

LIST OF REFERENCE SYMBOLS

110 Analytical magazine
112 First component
114 Outer circumferential side
116 Inner opening
118 Transport element
119 Notches
120 Receptacles
122 Chambers
124 Annular groove
126 Openings
128 Test element openings
130 Sampling openings
132 Actuator openings
134 Analytical aids
136 Lancets
137 Capillary channel
138 Lancet end
140 Lancet body
141 Coupling elements
142 Metal disk
144 Holding element
145 Positioning openings
146 Connecting elements
147 Tapered portions 148 Second component
150 Depressions
152 Ribs
154 Transfer openings
156 Housing
158 Test chemical
160 Test chemical field
162 Chemical ring
164 Carrier
166 Seal
168 Region facing the chambers
170 Test fields

What is claimed is:

1. An analytical magazine comprising a plurality of analytical aids received in chambers, wherein the analytical magazine has at least one test chemical which is designed to change at least one measurable property in the presence of at least one analyte to be detected, wherein the at least one test chemical is applied to a continuous carrier and forms at least one test chemical field, wherein the test chemical field is an area coated with test chemical throughout and is provided jointly for a plurality of the chambers, wherein in each case at least one region of the test chemical field faces the interiors of the chambers and is accessible from inside the chambers, wherein the analytical magazine is made by a method comprising;
providing at least one first component of the analytical magazine, wherein the first component comprises a plurality of receptacles,
providing a plurality of analytical aids, wherein the analytical aids are connected to one another by means of at least one holding element,
introducing the analytical aids into the receptacles, wherein a plurality of the chambers are loaded simultaneously; and
separating the analytical aids from the holding element, and wherein the analytical aids are produced at least in part integrally with the holding element, wherein the analytical aids comprise lancets, micro-samplers, or lancets and micro-samplers,
wherein the analytical aids are worked from a basic material of the holding element, such that the holding element and the analytical aids or parts thereof are produced, wherein the basic material is a metallic basic material,
wherein the analytical magazine further comprises a housing with at least two components, wherein a first of the at least two components and a second of the at least two components have a different transparency, and wherein the at least two components have different absorptions in a spectral range of 700 to 1100 nm.

2. The analytical magazine according to claim 1 wherein the test chemical field is part of the housing.

3. The analytical magazine according to claim 1, wherein the housing comprises a material selected from the following materials: a polycarbonate; an acrylonitrile-butadiene-styrene; a cycloolefin copolymer; a polymethyl methacrylate; a polystyrene; and a polyethylene terephthalate.

4. The analytical magazine according to claim 1, wherein the analytical aids furthermore have at least one lancet with at least one capillary channel for receiving body fluid, which is conducted to the test chemical via the lancet.

5. The analytical magazine according to claim 4, wherein the capillary channel of the lancet is coated in order to enable improved transport of the body fluid.

6. The analytical magazine according to claim 2, wherein the test chemical field is part of an outer magazine housing wall.

7. The analytical magazine according to claim 1, wherein the analytical aids are arranged in a circular pattern such that tips of the analytical aids point radially outward from a center of the circular pattern.

8. The analytical magazine according to claim 1, wherein the analytical aids are mounted such that they are movable for a sampling movement.

9. An analytical magazine comprising a plurality of analytical aids received in chambers, wherein the analytical magazine has at least one test chemical which is designed to change at least one measurable property in the presence of at least one analyte to be detected, wherein the at least one test chemical is applied to a continuous carrier and forms at least one test chemical field, wherein the test chemical field is an area coated with test chemical throughout and is provided jointly for a plurality of the chambers, wherein in each case at least one region of the test chemical field faces the interiors of the chambers and is accessible from inside the chambers, wherein the analytical magazine has a housing with at least two components which are connected to one another by at laser welding seams having, widths of at most 0.3 mm.

10. The analytical magazine according to claim 9, wherein the test chemical field is part of the housing.

11. The analytical magazine according to claim 10, wherein the test chemical field is part of an outer magazine housing wall.

12. The analytical magazine according to claim 9, wherein the analytical aids comprise lancets, micro-samplers, or lancets and micro-samplers.

13. The analytical magazine according to claim 9, wherein the analytical aids are mounted such that they are movable for a sampling movement.

14. The analytical magazine according to claim 9, wherein the analytical aids are arranged in a circular pattern such that tips of the analytical aids point radially outward from a center of the circular pattern.

* * * * *

UNITED STATES PATENT AND TRADEMARK OFFICE
CERTIFICATE OF CORRECTION

PATENT NO. : 10,105,088 B2
APPLICATION NO. : 15/051274
DATED : October 23, 2018
INVENTOR(S) : Hans List et al.

Page 1 of 1

It is certified that error appears in the above-identified patent and that said Letters Patent is hereby corrected as shown below:

On the Title Page

Item [30], delete "Feb. 20, 2009" and insert therefor -- Feb. 19, 2009 --

Signed and Sealed this
Twenty-second Day of January, 2019

Andrei Iancu
*Director of the United States Patent and Trademark Office*